United States Patent
Narayan et al.

(10) Patent No.: US 7,123,954 B2
(45) Date of Patent: Oct. 17, 2006

(54) METHOD FOR CLASSIFYING AND LOCALIZING HEART ARRHYTHMIAS

(76) Inventors: Sanjiv Mathur Narayan, 8520 Costa Verde Blvd, #3422, San Diego, CA (US) 92122; Valmik Bhargava, 2757 Schenley Ave., San Diego, CA (US) 92122

(*) Notice: Subject to any disclaimer, the term of this patent is extended or adjusted under 35 U.S.C. 154(b) by 239 days.

(21) Appl. No.: 10/323,423

(22) Filed: Dec. 18, 2002

(65) Prior Publication Data

US 2004/0059237 A1    Mar. 25, 2004

Related U.S. Application Data

(60) Provisional application No. 60/412,148, filed on Sep. 19, 2002.

(51) Int. Cl.
*A61B 5/046* (2006.01)
(52) U.S. Cl. .................................................... 600/518
(58) Field of Classification Search ................ 600/509, 600/515–518, 523
See application file for complete search history.

(56) References Cited

U.S. PATENT DOCUMENTS

| | | | | | |
|---|---|---|---|---|---|
| 5,215,098 A | * | 6/1993 | Steinhaus et al. | ........... | 600/515 |
| 6,016,442 A | * | 1/2000 | Hsu et al. | .................. | 600/518 |

* cited by examiner

*Primary Examiner*—Kennedy Schaetzle
(74) *Attorney, Agent, or Firm*—Stout, Uxa, Buyan & Mullins, LLP

(57) ABSTRACT

Analyzes surface electrocardiographic and intracardiac signals to identify and separate electrical activity corresponding to distinct but superimposed events in the heart. Assesses the spatial phase, temporal phase, rate, spectrum and reproducibility of each event to determine uniformity of activation in all spatial dimensions. Uses numerical indices derived from these analyses to diagnose arrhythmias. Uses these indices to determine the location of an arrhythmia circuit, and to direct the movement of an electrode catheter to this location for ablation or permanent catheter positioning. Subsequently, uses these indices to determine whether ablation has successfully eliminated the circuit. Uses variability in these indices from the surface electrocardiogram to indicate subtle beat-to-beat fluctuations which reflect the tendency towards atrial and ventricular arrhythmias.

61 Claims, 15 Drawing Sheets

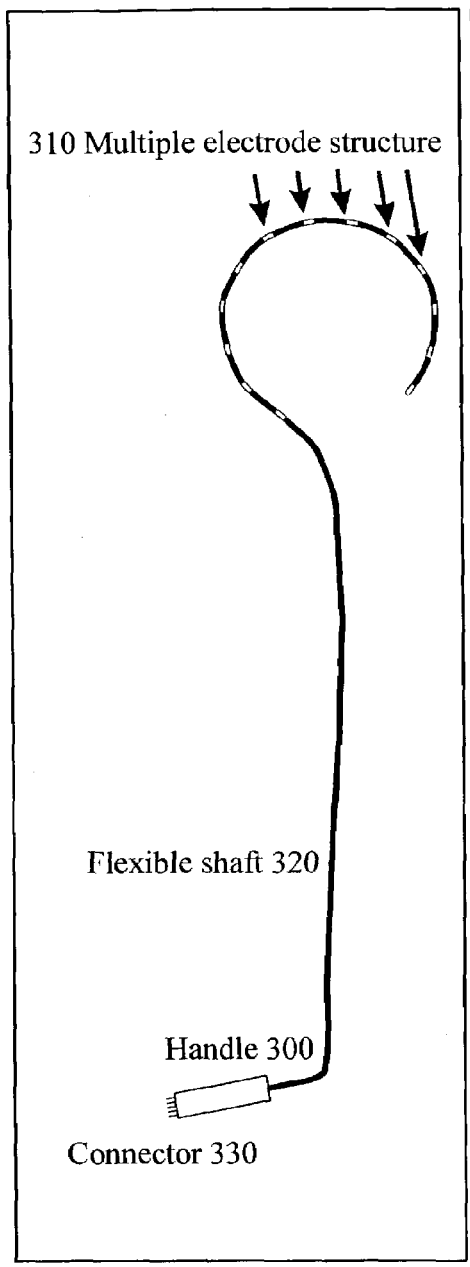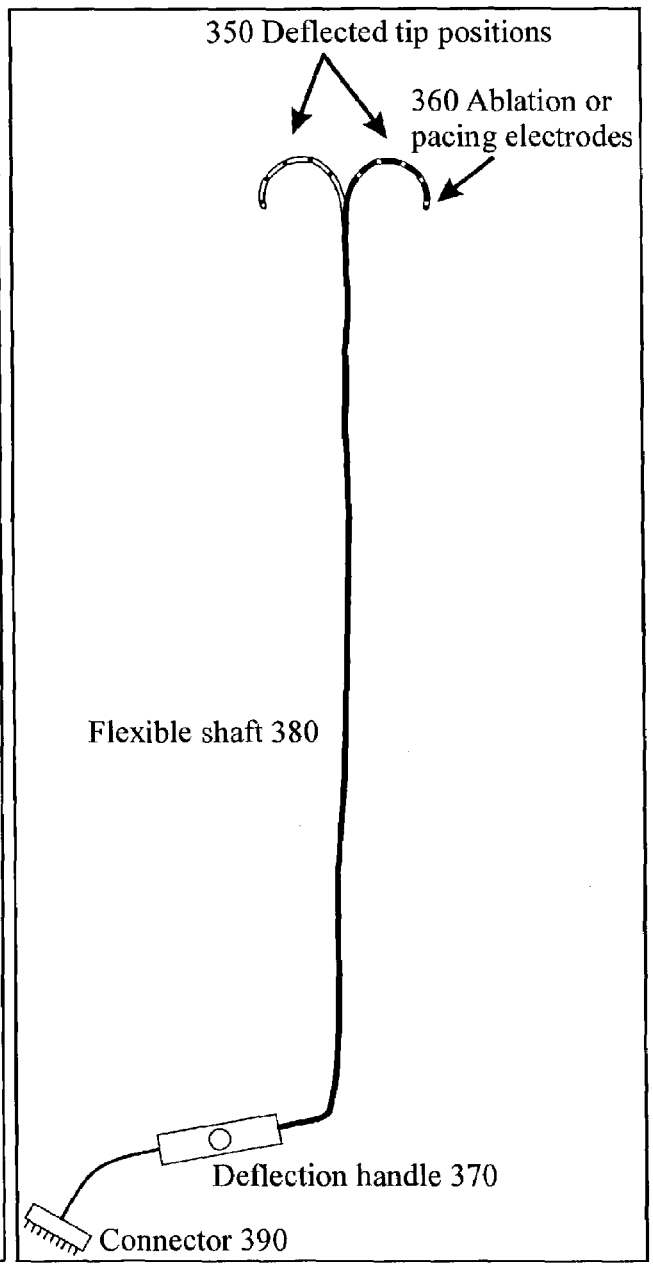
Figure 2
Halo catheter
Figure 3
Ablation Catheter

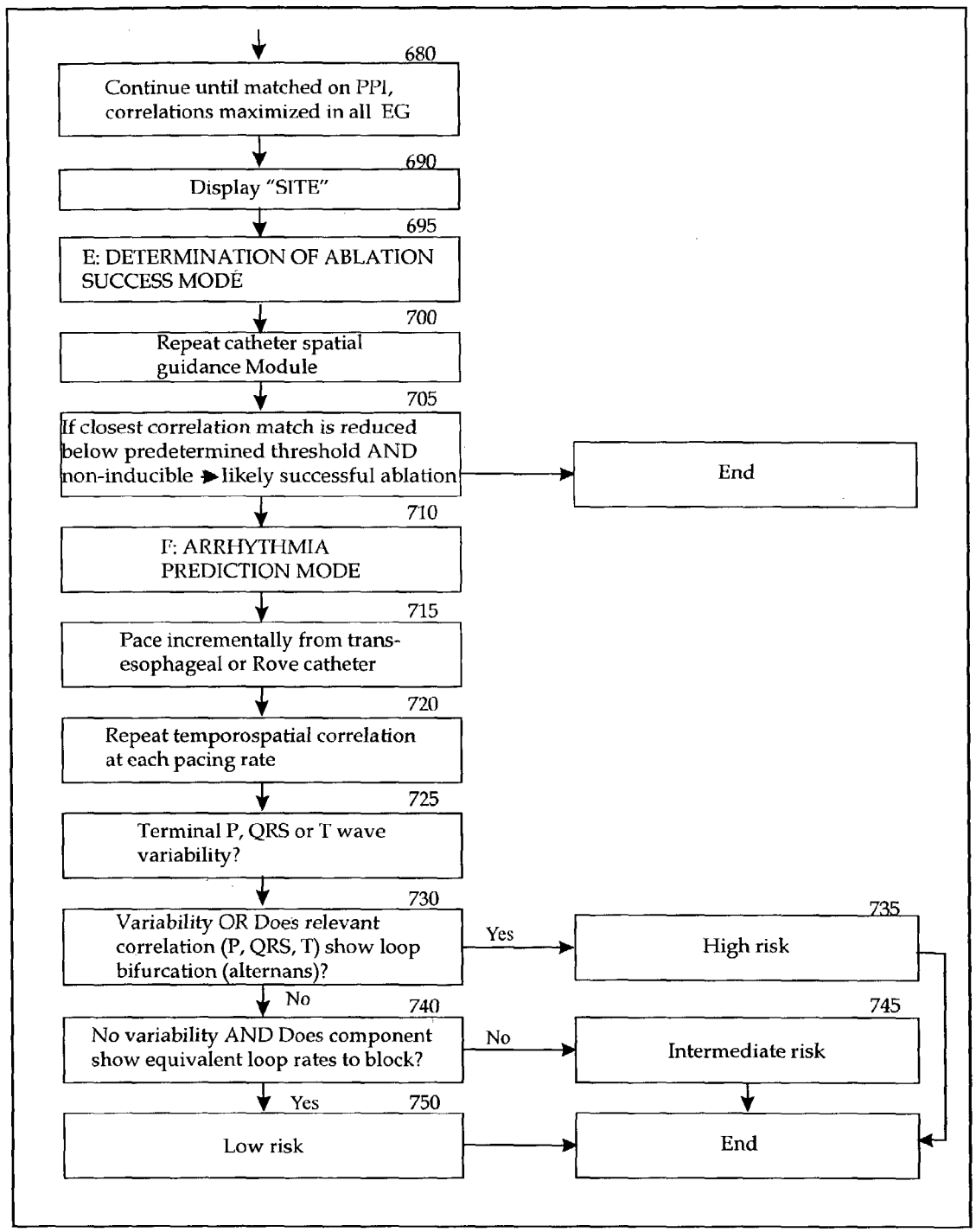
Figure 4 (contd.)

METHOD FOR CLASSIFYING AND LOCALIZING HEART ARRHYTHMIAS

This application claims the benefit of U.S. Provisional Application No. 60/412,148, filed Sep. 19, 2002, the entire contents of which are incorporated herein by reference.

BACKGROUND OF INVENTION

Field of the Invention

This invention relates generally to the field of heart rhythm disorders and more specifically to systems and methods for analyzing the electrocardiogram, pacing and mapping the heart for the diagnosis and treatment of cardiac conditions.

HISTORY OF TECHNOLOGY

A normal heartbeat consists of an organized sequence of conduction and orderly myocardial contraction. Normal (sinus) rhythm begins when the sinoatrial node (or "SA node") generates a depolarization wavefront in atrium. The impulse causes adjacent atrial cells to depolarize in a spreading wavefront, resulting in the "P-wave" on the Electrocardiogram (ECG), which causes the atria to contract and empty blood into the ventricles. Next, the impulse is delivered via the atrioventricular node (or "AV node") and the bundle of His to myocardial tissue cells of the ventricle. Depolarization propagates similarly across ventricular cells, resulting in the "QRS" complex on the ECG, causing the ventricles to contract and eject blood into the lungs and the systemic circulation.

Unfortunately, several important and common diseases result when aberrant conductive pathways develop and disrupt the normal paths of atrial or ventricular depolarization. In general, anatomic barriers (known as "conduction blocks") can develop and disorganize the electrical impulse into wavelets that circulate around the barrier. In addition, localized regions of scarred or ischemic tissue may propagate depolarization slower than normal tissue, causing "slow conduction zones" (SCZ) which facilitate the wavelets to create errant, circular propagation patterns. The "reentry" or "circus motion" resulting from these effects disrupts normal depolarization and contraction of the atria or ventricles, and can lead to abnormal rhythms ("arrhythmias").

Arrhythmias cause significant mortality and morbidity in the United States. Arrhythmias can include fast rhythms ("tachycardias") and slow rhythms ("bradycardias"). Both can be life-threatening or cause symptoms such as shortness of breath, chest pain, dizziness, loss of consciousness or stroke. Ventricular arrhythmias are the most common cause of sudden death, causing over 300,000 deaths per year. Ventricular arrhythmias include ventricular tachycardia (VT) and fibrillation (VF). Atrial arrhythmias are very common and cause many symptoms. They include atrial fibrillation (AF), the most common arrhythmia in the U.S., affecting up to 5% of the population, atrial tachycardia (AT) and atrial flutter (AFL).

Accurate and precise diagnosis of the arrhythmia is critical in customizing medication therapy for the patient, and to provide accurate advice on the likely outcomes of therapy for that patient. In addition, many arrhythmias are cured nowadays by precisely destroying tissue (known as "ablation") responsible for aberrant conduction using a specialized electrical probe (or "catheter"). For example, typical atrial flutter, in which the circuit involves the sub-eustachian isthmus of the right atrium, is successfully cured in this way. However, other rhythms that may appear similar on the surface ECG, such as atypical AFL, may involve circuits that vary between successive beats and may not consistently involve the isthmus. These rhythms are less successfully ablated. The precise diagnosis and localization of the tissue responsible for an arrhythmia is clearly important for successful ablation.

1. Diagnosis

Current techniques for precise heart rhythm diagnosis are sub optimal and cumbersome. Although the electrocardiogram (ECG) recorded from the body surface forms the cornerstone of diagnosis, current interpretation methods often cannot determine the arrhythmia diagnosis. Invasive electrophysiologic study is then required to confirm the diagnosis and decide upon treatment, although this involves discomfort and risk to the patient. For example, the ECG often cannot separate typical and atypical AFL. However, this distinction is important since typical AFL is best treated by ablation while atypical AFL is more difficult to ablate and is often treated with medications. Thus, invasive electrophysiologic study may be performed, only to find atypical AFL and recommend drug treatment. There is a pressing need to improve upon the prior art and allow accurate diagnosis from the standard 12-lead body surface ECG of the various forms of AFL, other atrial arrhythmias and forms of VT.

2. Arrhythmia Localization, Catheter Guidance and Determination of Ablation Success For successful ablation, destructive energy is typically targeted and delivered using a catheter positioned in contact with tissue integral to the circuit. The first pass at arrhythmia localization is made using the ECG. However, current methods of analyzing the ECG are often inadequate even to determine if the rhythm originates in the atria or ventricle (such as "wide complex tachycardias"), or whether it primarily involves the left or right side of the heart (such as atypical AFL). However, these distinctions are important since they determine the recommendation for medical or invasive therapy, and the type of invasive therapy (including ablation or surgery). There is a real need for methods to improve arrhythmia localization from the ECG, to help avoid electrophysiologic study in some patients while guiding the study in others.

More precise arrhythmia localization is usually performed during invasive electrophysiologic study. These methods generally involve placing a catheter close to the arrhythmia circuit. This is indicated when the signals after stimulating the heart ("pacing") match those during the actual arrhythmia. However, this requires considerable skill and is often cumbersome even for practitioners skilled in the prior art. All methods require the physician to assimilate and compare the shape and relative timing of multiple (often 10–15) complex signals from the ECG and inside the heart ("intracardiac"), during each pacing episode. This is a field in which numerical and computer processing should have led to increased precision and efficiency. However, the prior art has yet to fill this void; most practitioners use their expert knowledge to process information in much the same way as they did a decade ago.

Once a catheter is maneuvered to the located arrhythmia circuit, it is used to deliver destructive energy ("ablation"). Determining whether ablation is successful is also sub optimal. It requires the physician to be unable to re-induce the arrhythmia. However, this is not foolproof since many arrhythmia circuits are induced on a sporadic basis in the first place. There is clearly a need for quantitative methods to reproducibly determine if activation of the arrhythmia circuit has been eliminated by ablation.

3. Pacemaker and Defibrillator Lead Positioning

The leads of pacemakers and implantable defibrillators are required to pace or deliver high-voltage energy to ("defibrillate") a heart chamber. This purpose is best served by placing leads close to arrhythmia circuits. However, this customization for each patient is not performed, and leads are generally placed in standard anatomic locations. This is because current methods for arrhythmia localization are difficult to implement when implanting a lead. Therefore, even though an atrial lead would better terminate AFL, for example, if placed in the right atrial isthmus, it is usually placed in the right atrial appendage. Similarly, the ventricular lead of an implantable cardiac defibrillator is rarely targeted to a site of VT, even though pacing and defibrillating rhythms emanating from that site may be the main function of that device.

A method to quickly and systematically localize an arrhythmia circuit during implantation of a pacer or defibrillator lead would significantly advance the performance of each of these frequently implanted devices.

4. Arrhythmia Risk Stratification

The prediction of whether a patient will develop an arrhythmia in the future is becoming increasingly important. This is particularly true for VT and VF, where the first occurrence may cause death, but is also important for AF and other arrhythmias. However, the current art is sub optimal in this "risk stratification" since it is rarely able to detect substrates until the patient has a documented arrhythmia. Although there are several methods to determine the risk for VT or VF, none are very accurate and they have not entered routine clinical practice. The prior art for predicting AF, AFL and other atrial arrhythmias is even more rudimentary.

There is a very real need to improve risk stratification for these arrhythmias. Waiting for VT or VF to occur puts the patient at an unacceptable risk (a third or more will not survive), but if identified ahead of time they may receive proven life-saving treatment such an implantable cardioverter defibrillator. Similarly, waiting for AF or AFL to occur delays treatment, while earlier diagnosis and treatment makes them less likely to progress and reduces the risk for stroke and other complications.

PRIOR TECHNOLOGY

This section will describe prior technology in each of the areas covered by the invention.

1. Diagnosis

The surface ECG is by far the most common technology used by skilled practitioners to diagnose an arrhythmia. The prior art describes several methods to use the ECG to broadly classify rhythms including AF, typical or atypical AFL, VT or VF. However, these methods are limited when attempting to separate related rhythms, such as AF or AT from AFL as shown by Horvath et al. [1], or when more precisely localizing atrial [2] or ventricular circuits.

Several methods can improve ECG diagnosis of atrial rhythm events by enhancing P-wave detection. These include methods to subtract out the QRS complex including U.S. Pat. No. 4,721,114 issued to DuFault and work by Xue et al. [3]. However, these methods simply enhance atrial activity. Fast atrial rates are likely to signify AF. This can be detected via frequency analysis of the surface ECG, as in U.S. Pat. No. 6,064,906 issued to Langberg. The shape of the P-wave can also help localize sites of origin in the atria, such as work by Tang et al. [2], and pulmonary veins [4]. Recent methods have used high spatial resolution body surface potential maps to improve the non-invasive detection of atrial activation and its vector of activation, such as work by SippensGroenewegen et al. [5].

Several methods have been used to diagnose ventricular arrhythmias from the ECG. The most frequently used prior art includes the criteria of Brugada et al. [6] to separate VT from types of atrial arrhythmia that appear similar. If a beat is thought to arise from a ventricular site, ECG vector analysis can determine the location of that site [7]. Finally, high spatial resolution ECGs have also been used to better define the direction of activation in VT, such as work by Peeters et al. [8].

Currently, when a definitive diagnosis of an arrhythmia is required, intracardiac signals have to be analyzed. Such signals are obtained at invasive electrophysiologic study, which introduces discomfort and potentially serious risks to the patient. At invasive study, signals are recorded from each chamber of the heart, enabling their relationship to be easily determined. Notably, most of the prior art focuses on diagnosis using the ECG or intracardiac signals, but not both.

Using intracardiac atrial and ventricular signals, much of the prior art focuses on detection of high rates. AF has been diagnosed from high atrial rates in U.S. Pat. No. 5,522,852 issued to White, U.S. Pat. No. 6,041,251, issued to Kim and U.S. Pat. No. 5,827,197 issued to Bocek. High rates are also analyzed as high frequencies in U.S. Pat. No. 6,178,347 issued to Olsson. In particular, work by Stambler et al. [9] showed that, after QRS subtraction, AF is represented by several frequency components in a broad bandwidth. U.S. Pat. No. 5,868,680 issued to Steiner reports that when AF becomes more organized, indicated by distinct frequency characteristics, it is more likely to terminate. Other work, such as U.S. Pat. No. 5,366,486 issued to Zipes and U.S. Pat. No. 5,509,925 issued to Adams, used signal regularity to diagnose AF and make similar inferences.

AF and AFL have also been diagnosed using variability in the size or shape of atrial signals on intracardiac tracings. AF is associated with a fall in intracardiac atrial signal size in U.S. Pat. No. 5,720,295 issued to Greenhut, while atrial signal shapes distinguish AFL (consistent) to AF (variable) in U.S. Pat. No. 5,968,079 issued to Warman. However, much of this work cannot separate typical from atypical AFL, which have similar rates and ECG appearances, but different treatments. U.S. Pat. No. 5,782,876 issued to Flammang and other work use rules based on the rate and regularity of intracardiac atrial signals to separate AF from AFL. As a means to separate atypical AFL from AF, which can be difficult from the ECG, U.S. Pat. No. 5,817,134' issued to Greenhut diagnosed AF when variability between 2 temporally or spatially separated atrial signals is high. U.S. Pat. No. 5,676,153 issued to Smith extends this concept by measuring the distance over which atrial signals are part of the same wavefront ("activation space constant"), thus separating AFL (most organized) from AF (least organized).

Intracardiac diagnosis can also be based on the relationship between atrial and ventricular activity (atrioventricular relationship), such as U.S. Pat. No. 5,782,876 issued to Flammang, while U.S. Pat. No. 5,542,430 issued to Farrugia and other work describes how this relationship can be analyzed using neural networks.

Analogous prior art pertains to ventricular rhythm diagnosis. For the surface ECG, VT and VF can be detected from a rapid rate, from wide QRS complexes in U.S. Pat. No. 5,400,795 issued to Murphy, and via measures of ECG complexity in work by Zhang et al. [10]. Using intracardiac signals, VT and VF have been detected from rapid ventricular signals in U.S. Pat. No. 5,891,170 issued to Nitzsche, signal shapes in U.S. Pat. No. 4,552,154 issued to Hartlaub, and systems that integrate many such criteria such as U.S. Pat. No. 5,542,430 issued to Farrugia.

2. Arrhythmia Localization and Ablation

Two major concepts in the prior art help localize an electrode close to the arrhythmia circuit, to enable ablation or termination of the rhythm via pacing. First, pacing from the site of the arrhythmia will produce a theoretically identical ECG to the tachycardia. This "pace mapping" is used at invasive electrophysiologic study when the patient is not in the arrhythmia [11], and is described in the section entitled Detailed Description of the Invention. Second, a catheter placed at the arrhythmia site will record identically timed intracardiac signals and ECGs during tachycardia and when pacing. This "entrainment with concealed fusion" is used when the patient is in arrhythmia and works for both atrial [12] and ventricular [13] rhythms, and is also described further in the Detailed Description of the Invention. Although this approach is the standard of care, it accurately identifies the site to ablate in only 25% of ventricular [13] and 50% of atrial [12] rhythms. This shows the obvious difficulty for even the most skilled practitioners to compare differences between 10–15 waveforms from multiple catheter sites using just visual analysis.

3. Assessment of Ablation or Termination Effectiveness

There are very few methods in the prior art to determine if an arrhythmia has been ablated successfully. In the case of isthmus-dependent AFL, there are a few examples. First, work by Hamdan et al. [14] show that P-wave develops a specific shape and vector during isthmus pacing if ablation was successful. Second, a positive unipolar intracardiac signal on the opposite side of the ablation line to the pacing site [15] and, third, showing double potentials along the ablation line [16] indicate successful ablation. However, these methods are cumbersome and not always accurate, and practitioners often use the inability to re-start an arrhythmia to indicate that it has been eliminated; as discussed, this may be inaccurate if arrhythmia induction is sporadic.

4. Pacemaker and Defibrillator Lead Positioning

Placing a lead close to an arrhythmia site will make it easier to terminate that arrhythmia by pacing or defibrillation. The opposite is also true, and studies by Stevenson et al. [13] and Morton et al. [12] have shown that arrhythmias like AFL or VT are less easily terminated from a remote location. However, the prior methods for locating an arrhythmia (mentioned above) are lengthy and difficult to perform during permanent pacemaker or defibrillator lead implantation. However, targeting a specific lead position is increasingly felt to be important, and is already being done to improve the strength of heart contraction, such as work by Leclercq et al. [17], and possibly to reduce arrhythmias, in work by Zagrodzky et al. [18].

5. Arrhythmia Risk Stratification

There are several prior art methods to stratify the risk for arrhythmias non-invasively from the ECG. However, they can have limitations and are rarely used except for research. To predict AF, work by Steinberg et al. [19] and others show that prolonged atrial activity indicates slow conduction and may predict AF, while recent work by Narayan et al. [20] suggests that an alternation of the timing, shape or amplitude of the intracardiac atrial signals may predict AF. In the ventricle, Kleiger et al. [21] showed that reduced variability over 24 hours in the interval between heart beats ("heart rate variability") predicts VT or VF. Slow conduction through ventricular scar has been detected as "late potentials" at the end of ventricular depolarization, and may predict the risk for ventricular arrhythmias [22]. U.S. Pat. No. 4,802,481 issued to Cohen, and work by others, describe techniques for using fluctuations in the size of T-waves ("T-wave alternans") to predict VT or VF. Newer methods, such as U.S. Pat. No. 5,555,888 issued to Brewer use altered ventricular activation after sub-threshold current to assess the risk for VT or VF.

DEFICIENCIES IN PRIOR TECHNOLOGY

The prior art can have several significant deficiencies in each of the areas addressed by the current invention. Most prior art in the field of arrhythmias has limited scope. Thus, methods exist that can use either the surface ECG or intracardiac signals, but few that can use both. Similarly, there are several methods that apply for either atrial or ventricular arrhythmias, but few that apply to either. Furthermore, there are several methods that can examine the timing, spectra, spatial pattern or shape of ECG or intracardiac signals, but few that incorporate all four. This lack of integration has arisen since methods focus on the manifestations of arrhythmia substrates, rather than on the substrates themselves. This has slowed technical advances in arrhythmia management, since ECG diagnosis, arrhythmia localization and catheter guidance have had to be separated. In contrast, the current invention studies temporal, spatial phase and spectral relationships that are true for surface ECG and intracardiac signals, and for atrial as well as ventricular arrhythmias.

1. Diagnosis

Several specific deficiencies can be identified in the prior art. In general, the prior art focuses on arrhythmia diagnosis for implanted pacemakers and defibrillators, rather than on bedside clinical diagnosis.

First, the prior art does not help very much in separate rhythms of similar rate and regularity from the ECG. This remains a major dilemma since, for example, typical and atypical atrial flutter (AFL) may co-exist as described by Horvath et al. [1]. Ablation of typical AFL in these cases is less successful. If co-existence was known in advance, invasive study and its attendant risks may be avoidable. Another example is the diagnosis of a wide complex tachycardia as either VT or SVT, despite the rules proposed by Brugada et al. [6].

Second, the prior art has limited methods for analyzing superimposed activity. The method of QRS subtraction is frequently applied to 'uncover' P-wave activity, yet it introduces errors since the average QRS used for subtraction will differ from the actual QRS complex. These errors are often compounded if frequency analysis is subsequently performed.

Third, the prior art is poor at localizing an arrhythmia site from the surface ECG. The work by Tang et al. [2] and Yamane et al. [4] for atrial, and Callans et al. [7] for ventricular, arrhythmias provide very general locations. For example, they cannot determine if an atypical AFL circuit is in the right or left atria, which require significantly different invasive approaches.

Fourth, the prior art does not fully exploit functional information, such as whether atrioventricular relationships are likely physiologic. Thus, although methods have recently begun to focus on atrial versus ventricular rate, they usually ignore additional information used by experts, such as the precise timing of ventricular to atrial activity (for example, in atrial flutter with 4:1 ventricular conduction, does ventricular activity arise at the same point in each preceding atrial activity?)

Clearly, there is a need to improve the accuracy of ECG diagnosis of complex rhythms. Some of the uses of this improvement would be to improve the diagnosis and treatment of patients by physicians, improvements in the diagnostic algorithm of modem ECG machines, and a more solid foundation for invasive electrophysiologic studies in those patients who still require them.

2. Arrhythmia Localization and Catheter Guidance

Despite the current focus on ablation (destroying) many arrhythmia circuits using precisely targeted energy delivery, localization of the delivery site requires several manual measurements and comparisons by the practitioner. Very few methods have been described to automate or simplify this process. Ablation therefore remains time-consuming and laborious, even for the most skilled practitioners of the art.

From the ECG, the prior art for localization is limited. In the atrium, certain rhythms have characteristic ECG patterns, and ablation is successful using a stereotypical approach in most patients. Once the diagnosis of typical isthmus dependent AFL has been made, ablation in the isthmus of the right atrium is successful in the vast majority of cases as shown by Feld et al. [23]. Similarly, once the diagnosis of atrioventricular nodal reentry tachycardia is made, ablation in the region of Koch's triangle is almost universally effective as shown by Jackman et al. [24]. However, problems still arise when ECG patterns are not typical, such as atypical AFL masquerading as typical [1], or when another rhythm event mimics these ECG patterns. Ventricular arrhythmias are somewhat better localized from the ECG, but methods are still limited. First, certain ventricular rhythms have stereotypical ECG patterns, such as VT arising from the outflow tracts of the right or left ventricles as described by Callans et al. [7]. Second, vector analysis of ventricular complexes localizes the arrhythmia more easily than for atrial arrhythmias, where low voltages obfuscate this analysis. However, precise localization remains difficult and there are few tools enabling this task to be automated in modern ECG machines or laboratory electrophysiology systems.

In other rhythms, intracardiac localization must be customized to the patient using pace mapping or entrainment with concealed fusion. There is little prior art to aid or automate this cognitive process. This is true despite the widespread adoption of digital laboratory electrophysiologic machines, which therefore remain little more than digital monitors and recorders, annotation pads, measurement systems and storage devices.

Using catheters inside the heart, an arrhythmia circuit is located by finding the region which activates first, or from where pacing produces electrograms similar in shape to the tachycardia in all channels, known as pace mapping [11]. Methods have begun to numerically analyze beat similarity by storing a template (of native or paced rhythm), as described by Watanabe [25] and Saba [26], then performing a correlation of this beat to an aligned paced beat. However, these methods are limited. First, many different paced beats may produce the same numerical correlation against template, and therefore be indistinguishable. Prior methods do not identify which of these pacing sites is most likely to lead to successful ablation. Second, most strategies rely on a "lead count" of successful ECG lead matches (typically, "pacing matches tachycardia in 11/12 leads"). However, quite distinct pacing sites may produce matches in the same proportion of leads. The prior art does not identify which site is likely closest to a successful ablation site. Third, the prior art usually analyzes very few paced beats (often one), as discussed by Saba [26], which may be subject to "impurities". For example, this beat may be fused with native activation, making the pace maps appear better than they are. By way of another example, the beats analyzed may not adequately represent normal beat-to-beat variability, leading to the mis-classification of beats. Fourth, the prior art superimposes the paced and native beat to compute correlation at one "optimal" alignment. This single analysis for each beat ignores variabilities along the duration of the ECG beat. Fifth, the prior art correlation methods are greatly affected by amplitude or temporal scaling. In other words, paced and native beats of the same shape, but differing either in magnitude or "stretched" relative to the other, will not match well. As a corollary, the prior art is not effective when comparing rhythms of different rates, from different recording sessions or from different equipment. This prevents comparison of one rhythm to a previously stored rhythm in that patient or another patient. Sixth, the prior art provides little aid in guiding a catheter from its current position to move closer to the putative ablation site.

"Entrainment with concealed fusion" is used to confirm the diagnosis of re-entry and that an intracardiac catheter is located close to the circuit, as described by the prior art of Waldo [27, 28], Stevenson [13] and others. During tachycardia, several criteria must be met while pacing from the intracardiac catheter. First, the interval separating the intracardiac signal at the catheter from its ECG activity must be identical during pacing or tachycardia. Second, the ECG resulting from pacing (pace maps) should be identical to those during tachycardia. Third, after the cessation of pacing, the tachycardia should resume at its prior rate without an intervening delay. Fourth, progressively faster pacing should cause a progression in ECG and intracardiac signal shape from the tachycardia (when matched by the pacing rate) to that of pacing (when faster rates). Finally, the time interval between the pacing stimulus at the site and the ECG wave is characteristic.

However, the application of this method requires improvement. Although experts routinely apply these criteria for atrial [12] and ventricular [13] rhythms, their success in locating ablation sites is only 50% of atrial [12] and 25% of ventricular [13] rhythms. This highlights the difficulties for a human operator to compare subtle changes in the relative timing and shape of 12 surface ECG and additional intracardiac signals for each of several catheter positions, then select the set that matches the above criteria. Recently, concealed entrainment for a single beat was implemented by cross-correlation in U.S. Pat. No. 5,792,064 issued to Panescu. This prior art examined two criteria of concealed entrainment: whether intracardiac electrogram timing and shape were similar between one paced beat at the catheter location and the extra beat which initiates AF. However, this method was not described for continuous tachycardia. In addition, it did not analyze the surface ECG, nor did it assess the other criteria of concealed entrainment. Clearly, there is a need for numeric methods to implement this method and help to automate it.

3. Pacemaker and Defibrillator Lead Positioning

As mentioned above, positioning a pacemaker or defibrillator lead close to an arrhythmia circuit requires pace mapping or concealed entrainment. The current rules for these methods make them unwieldy to apply while placing a poorly steerable lead. There is a need to develop ECG methods, confirmed using intracardiac signals, to position a lead in an individualized location where it can later facilitate the termination of an arrhythmia by pacing (stimulating) or defibrillating (providing an electrical shock) the tissue.

4. Assessment of the Effectiveness of Ablation

There are few prior art methods to measure the effectiveness of ablation in eradicating the substrate for an arrhythmia. Although markers of success exist for certain arrhythmias, such as P-wave shape change and double potentials along the ablation line in AFL, most of the prior art does not probe the arrhythmia circuit and cannot therefore detect its absence after ablation. This may partly explain the recurrence rate after the ablation of AFL (up to 15%) and other rhythms. There is a need to accurately measure the continued presence of substrates for the arrhythmia.

5. Arrhythmia Risk Stratification

Risk stratification for arrhythmias from the surface ECG is an attractive but largely elusive task. Predicting the risk for AF remains difficult. There has been somewhat more success in predicting the occurrence of VT and VF. However, the "heart rate variability" method of Kleiger et al. [21] requires a long recording period, assesses only long-term risk, and cannot be performed in many patients with pre-existing arrhythmias such as AF. Late potentials cannot be examined if patients have AF or bundle branch block, and their predictive accuracy for VT or VF has also been seriously questioned. The "T-wave alternans" method of Cohen in U.S. Pat. No. 4,802,481 has sub optimal predictive accuracy and requires considerable experience in interpretation, yet still often produces uninterpretable results (see, for example, Bloomfield et al. [29]) and also cannot be performed if the patient has AF or bundle-branch block. The success of other, newer methods has yet to be determined. None have entered routine clinical practice as none improve upon assessments of the strength of ventricular contraction and other non-arrhythmic factors. There is clearly a need to improve the risk stratification for both atrial and ventricular cardiac rhythm events from the ECG.

BRIEF DESCRIPTION OF THE DRAWINGS

FIG. 2 is a diagram of sensing/pacing a catheter in accordance with the present invention;

FIG. 3 is a diagram of sensing/pacing an ablation catheter in accordance with the present invention;

DETAILED DESCRIPTION OF THE INVENTION

Figure 1A:
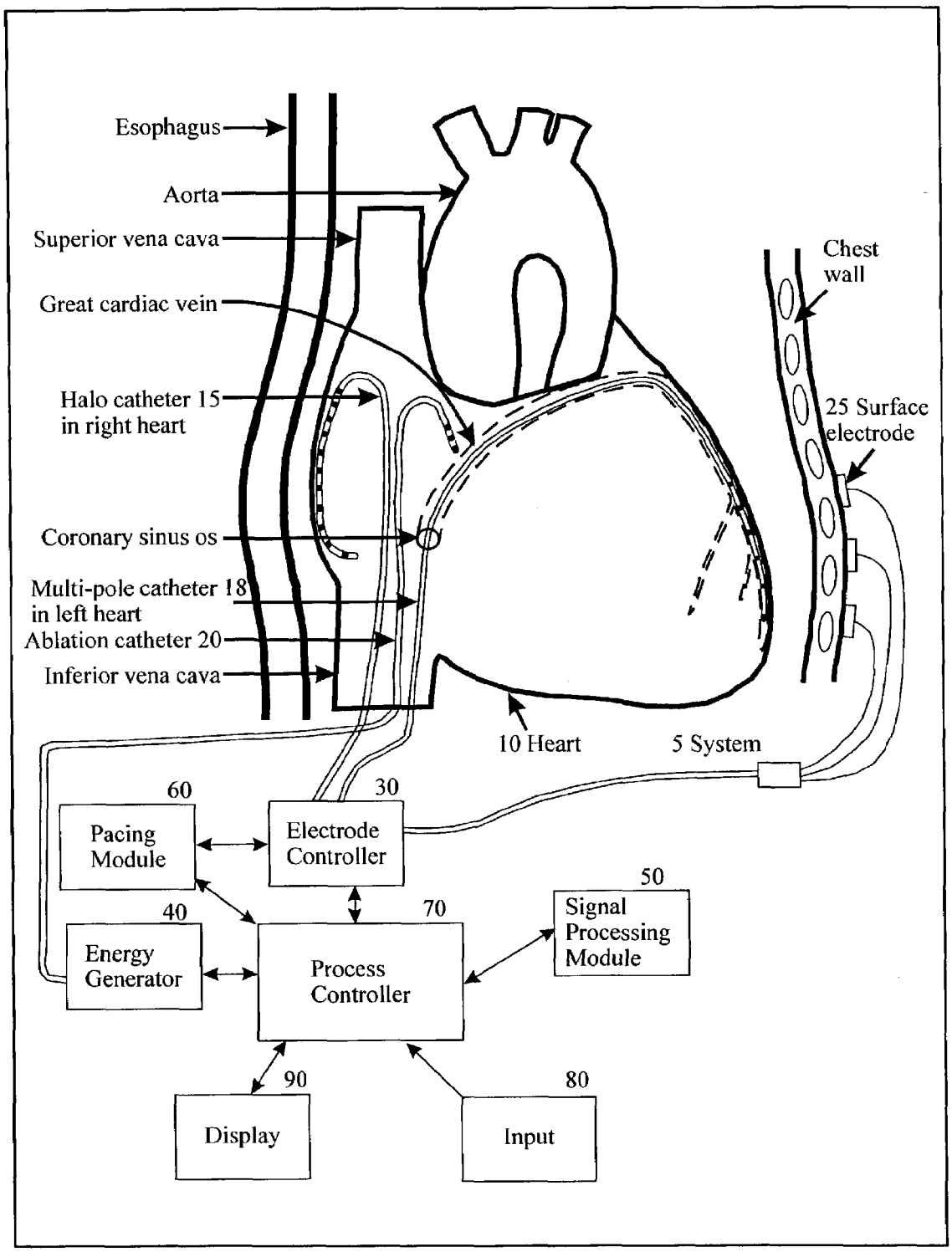
FIG. 1a is a general schematic of a system in accordance with the present invention.

FIG. 1A shows an overview of the general components of a system 5 for analyzing the timing and shape ("morphology") of body tissue biopotentials in three spatial dimensions over time, for diagnostic and therapeutic purposes. The heart is shown diagrammatically and not in an anatomically accurate form. The illustrated and preferred embodiment shows the system being used to analyze the activation ("depolarization") and recovery ("repolarization") of heart tissue experiencing an arrhythmia.

A strength of this invention is that it has the option of integrating the analysis of shape, distribution, reproducibility and timing of biopotentials from inside the heart as well as from the body surface. From the surface ECG, the invention can analyze a cardiac signal which corresponds to the activation wavefront on the heart, and which can be measured using several ECG leads. The invention can diagnose subtly different rhythm abnormalities ("arrhythmias") in the atria and/or ventricles from the traditional 12-lead ECG. This includes a very accurate separation between typical and atypical forms of atrial flutter (described above). Using spectral, temporal and spatial ECG morphology analysis, the invention can precisely compare pace-maps taken from different locations and times in a single patient, or compare them to previously stored ECG maps of known arrhythmias from this or different patients. Pacing can be performed using a medical instrument including, but not limited to devices inside the heart, e.g., pacing catheters, pacemaker leads and defibrillator leads, or devices external to the heart. The invention also performs non-invasive prediction of the presence of substrates for arrhythmias by detecting variations in the above analysis from beat to beat.

From signals inside the heart ("intracardiac"), the invention quantifies the measurement of entrainment with concealed fusion [12, 13]. This enables it to confirm an ECG diagnosis, and to help automate the diagnosis of an arrhythmia mechanism and its localization, to enable a catheter to be placed close to the circuit for therapeutic ablation. The invention provides a spatial relationship comparator function, enabling it to guide the physician in moving a catheter towards the arrhythmia circuit for optimum ablation. The invention can also be used for the optimal placement of a pacemaker or defibrillator lead. Finally, the invention can assess whether ablation was successful by detecting whether substrates for the arrhythmia circuit are still present.

The invention is well suited for use in performing electrical diagnosis and therapy of the heart. However, it should be appreciated that the invention is applicable for use in other regions of the body where tissue biopotential morphologies can be ascertained by analyzing electrical events in that tissue. For example, the various diagnostic aspects of the invention have application in analyzing electroencephalograms in the brain or neurologic tissue, or electrograms in the gastro-intestinal tract. Many aspects of the invention have potential applicability for invasive surgical techniques on the heart, brain or other organs. Furthermore, it should be appreciated that the invention can analyze any biopotential and could be applied, for example, to the detection of atrial and ventricular timing and hence the analysis of rhythm disturbances using hemodynamic recordings.

Furthermore, the principal analysis of this invention has potential applicability in the field of electrical engineering, such as to assess frequency variability ("jitter") from an oscillating waveform, such as may arise from analogue circuits. This will be discussed again later.

Turning in more detail to FIG. 1A, one can see the system 5 for analyzing electrical events in the heart 10 using a combination of electrodes. These electrodes may be standard body surface ECG electrodes 25, or electrode catheters placed within the chambers or vasculature of the heart, labeled 15, 18, 20. An ablation catheter 20 can be placed within the heart or its vasculature to destroy tissue responsible for a cardiac event. From a general point of view, it can be seen that the electrodes interface with an electrode controller 30, interfaced to a process controller 70. The ablation catheter 20 interfaces with an energy generator 40. The process controller 70 interfaces to modules for signal processing 50, pacing 60 and the energy generator 40. The process controller 70 also receives input from an input module 80 and controls a display module 90.

Figure 1B:
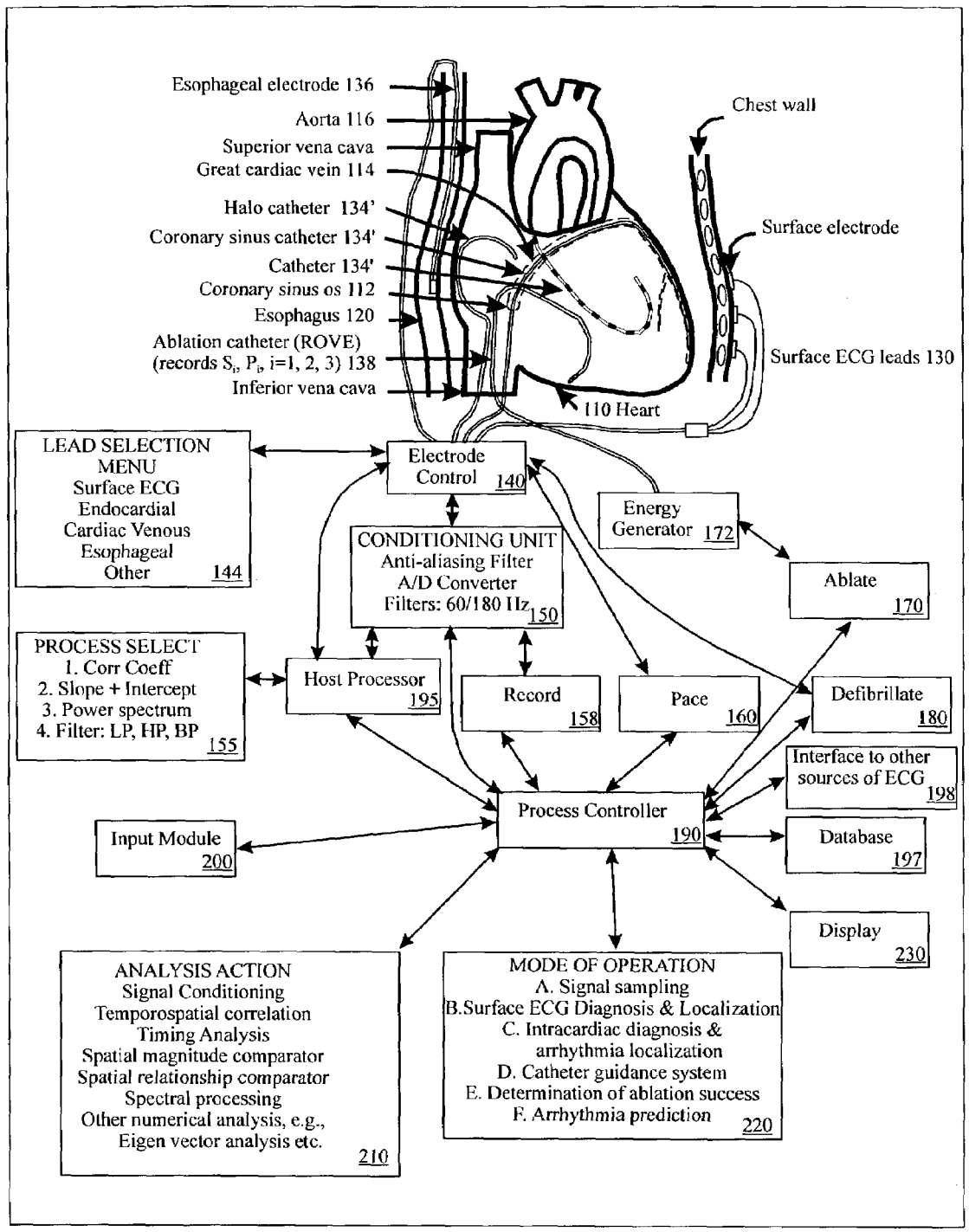
FIG. 1b is a detailed schematic of the system of the present invention.

FIG. 1B presents a detailed schematic of a preferred embodiment of the invention. The system analyzes electrical events in regions of the heart 110. Signals may be recorded from standard body surface ECG electrodes 130, catheters 134' percutaneously inserted into a vein or artery (typically the femoral vein or artery) into the right or left side of the heart, or inserted into the coronary arteries (not shown) via the aorta 116 by passing retrograde from a peripheral artery, or through the coronary sinus 112 into the cardiac veins 114. An electrode 136 can also be placed within the esophagus 120, where it lies in close proximity to the heart without the need to directly access the vasculature. An important component is the connection of one or more ablation catheters 138. One of the above catheters, denoted ROVE, is moved within the heart to localize an arrhythmia circuit. In the preferred embodiment, ROVE is the ablation catheter 138, which is typically steerable and therefore easily directed within the heart 110 or its vasculature 114, but any catheter may serve this purpose. A series of signals recorded at ROVE during the cardiac diagnosis are labeled $S_i$, and during pacing are labeled $P_i$, where I=1, 2, 3 or greater. These signals S1, S2, S3 or P1, P2, P3 may represent signals obtained from one site at different timepoints, or from separate and distinct sites at one timepoint. In the preferred embodiment, these signals are unipolar recordings, obtained between ROVE catheter electrodes and a distant electrode in the inferior vena cava or another indifferent electrode (not shown). However, these and other signals may also be recorded in bipolar, monophasic action potential or other configurations as desired.

The electrodes are connected to an electrode control 140 allowing electrical stimulation of the heart from a menu of electrodes 144, at user-selectable current, voltage, waveform shape, rate and pattern of stimulation. This can be implemented using commercially available digital-to-analog processor boards and associated software such as those from National Instruments Inc., Austin, Tex. Signals from the electrode controller 140 pass through a conditioning unit 150 that includes an anti-aliasing filter, analog-to-digital converter and line frequency filter. A cardiac signal should first be digitized using this conditioning unit 150. The conditioning unit can also effectively removes pacing stimuli from the input waveform using smoothing, low-pass filtering, interpolation or other methods in a window centered on the stimulus artifact. The electrograms may or may not be filtered before analysis. Typically, a 0.05–300 Hz bandpass filter is used for filtering. If a filter is used to reduce the noise, the same filters must be employed for all subsequent analysis since filtering may alter electrogram morphology. In addition, magnitude clipping or clamping is made available to diminish the effect of large or outlying magnitudes on subsequent analyses. The ablation electrode 138, is connected to an energy generator 172. Typically, this provides radiofrequency energy such as that from EP Technologies Inc., Sunnyvale, Calif., but could alternatively provide electrical, ultrasound, infrared or other energy types.

For recording, conditioned signals are transferred to a recording system 158 comprising electromagnetic, magneto-optical or other technology. Signals are then processed on the host processor 195, such as a personal computer, using a menu 155. This menu includes mathematical processing for correlation, slope and intercept, and power spectral analyses, as well as additional filters such as high, low and band pass and notch. A pacing module 160 provides energy pulses to the electrode control system 140 to electrically stimulate the heart. A defibrillating energy source 180, such as that by Medtronic Physio-Control, Redmond, Wash., is used to cardiovert or defibrillate the heart using connections to the electrode controller 140 via catheters 134',136 or 138 or surface paddles. An ablation module 170 interfaces with the energy generator 172 interfaced to the ablation catheter 138.

To accomplish an important goal of the invention, a master process controller 190 integrates the abovementioned modules for recording 158, pacing 160, ablation 170 and defibrillation 180. The process controller 190 is electrically coupled by a bus to the host processor 195, that is adequately implemented as a Pentium II, Macintosh G-series or newer computer. The process controller 190 interfaces to a database system 197 for storage of electrograms and analyzed information, to alternative ECG sources 198, an input module 200 and a display module 230.

In an alternative embodiment, ECG and electrogram data can be uploaded from the database 197 for analysis in a completely analogous fashion to the real-time mode of operation described below. Data from the database 197 can be from the same or different patients, recorded at any time and using any acquisition system. In yet another embodiment, the process controller 190 can upload for analysis electrograms from a mapping system, that may be computed ("virtual"), such as in the system by Endocardial Solutions, Inc. (St. Paul, Minn.), or real, such as in the system by Biosense Webster, Inc. In these cases, the mapping system provides additional location information for these electrograms, which is used for subsequent catheter electrode localization.

The input module 200 allows selection of the mode of operation and other functions of the invention. In the preferred embodiment, a menu of Modes of Operation 220 includes A. Signal Sampling; B. Surface ECG Diagnosis and Localization, C. Intracardiac Diagnosis and Arrhythmia Localization, D. Catheter Guidance System to target the placement of a diagnostic, ablation, pacemaker or defibrillator electrode, E. Determination of Ablation Success after delivery of ablation energy, and F. Arrhythmia Prediction by detecting arrhythmia substrates prior to arrhythmia onset. In an alternative embodiment, these and related modes can be selected using a neural network or other type of expert system.

Analysis actions may be selected from a menu 210, either automatically or interactively by the user, and underlie each mode of operation. These analyses are described briefly now, and in more detail later in the specification. The first action includes further signal conditioning such as bandpass filtering. The primary analysis of this invention is the temporospatial correlation of electrogram morphology. This analyzes the reproducibility of electrogram morphology over time for each electrode, and then between electrodes. A strength of this method is that it can integrate analyses of the shape, distribution, reproducibility and timing of many types of biopotential. From the surface ECG, the analysis can diagnose regular versus irregular tachycardias, compare pace-maps, provide timing information similar to those from intracardiac signals and non-invasively determine the presence of arrhythmia substrates. From intracardiac signals, the system implements a quantitative measurement of entrainment with concealed entrainment including the matching of electrogram shapes. This enables it to make the diagnosis of reentry, place an electrode catheter close to an arrhythmia circuit for ablation or for pacemaker or defibrillator lead positioning, and to assess whether ablation was successful. Menu 210 provides additional analyses including Timing analyses, Spatial Magnitude comparator, Spatial relationship comparator, Spectral processing and other numerical methods including the computation of Eigen vectors, morphology cross-correlation, and magnitude clipping or clamping (which diminish the effects of large or outlying magnitudes).

The process controller 190 connects to a display module 230 to display user-selectable screens. Typically, information relevant to the current mode of operation is displayed, including real-time electrograms on all catheters including ROVE (mode A), the computed arrhythmia diagnosis (mode B) or intracardiac signals (mode C). The display also indicates the plane in which ROVE signals least match the arrhythmia under consideration. It therefore graphically displays the direction in which to move the ROVE catheter to reach the circuit (mode D). The display indicates if the ROVE catheter is close to a site where ablation is likely to terminate the arrhythmia, based on entrainment analysis, which is text labeled SITE (mode D). After ablation, the display indicates if ablation was likely to have been successful (mode E). Separately (mode F), the display indicates the presence of substrates for the arrhythmia for risk stratification. These display elements are enumerated by way of example, and several other items may be selected.

Although analysis actions 210 have been described as user-selectable choices, it must be stressed that the preferred embodiment is 'automated'. It suggests an optimal sequence of actions based on the current rhythm, and in this way integrates several of the above modes. The preferred embodiment therefore enables a complete and efficient arrhythmia diagnosis and therapeutic procedure for a patient. In a partly-automated fashion driven by user prompts and confirmations, the invention makes a diagnosis from the ECG and intracardiac signals, localizes the arrhythmia to facilitate ablation, then confirms its success.

FIG. 2 shows an electrode catheter (labeled 134' or 136 in FIG. 1B) with a flexible body 320. Its distal end carries a three dimensional multiple electrode structure 310. In one preferred embodiment of the invention, structure 310 takes the form of a linear array of electrodes. The shaft is approximately 100–125 cm in length, has an external diameter of 1–3 millimeters (3 to 9 "French"), and its terminal end may be straight or curved in various configurations. In another embodiment, structure 310 takes the form of a basket defining an open interior space. It should be appreciated that alternative one, two or three dimensional structures could also be used. A signal wire (not shown) is electrically coupled to each electrode in the multipole structure 310. The wires run through the flexible shaft 320 into a handle 300, and then to an external multiple pin connector 330. The connector 330 electrically couples the electrodes to the electrode controller 140 in FIG. 1B.

FIG. 3 shows an ablation probe that features a long narrow flexible catheter body 380. For the sake of illustration, FIG. 3 shows a single ablation electrode 360 at the distal tip of the catheter body 380. Of course, other configurations employing multiple ablation electrodes are possible. The ablation electrodes can be used to emit signals to pace the heart structure 110 (in FIG. 1B). A handle 370 attached to the proximal end of the catheter body 380 controls a steering mechanism that runs the length of the catheter, and bends or flexes the distal portion of the catheter body 380 along its length. This is shown in two positions 350. In the preferred embodiment, the tip can curve through an angle of curvature of approximately 180 degrees in each plane. The actual steering mechanism can vary, such as that described in U.S. pat. No. 5,254,088 issued to Lundquist, which is incorporated herein by reference. A wire (not shown) electrically couples the ablation electrode 360 to a connector 390. Connector 390 interfaces the electrode to an energy generator (172 in FIG. 1B) to provide varying types of energy to the electrode 360. Typically, the generator 172 supplies radio frequency energy, such as Model EPT-1000 from EP Technologies Inc., Sunnyvale, Calif. In use, the physician places the catheter 138 in contact with heart tissue at the site identified for ablation. The ablation electrode 360 emits energy to thermally destroy the tissue. Alternatively, a piezoelectric crystal-based catheter could generate ultrasound energy, while cells or genes could be injected to improve or worsen conduction.

In a preferred embodiment, the invention automatically runs a sequence of six modes that can be modified interactively by the user. The mode menu 220 can have different, fewer or greater number of modes. By way of example, a user can select Mode A, signal sampling, from the mode menu 220 on display 230 so that this mode is operated first. Upon completion of the mode, the user is prompted to either automatically enter Mode B or, for example, to return to the mode menu 220. While in Mode A, if a rapid arrhythmia ("tachycardia") is detected by the process controller 190, it thus prompts the user to initiate mode B: Surface ECG Diagnosis and Localization, that suggests the most likely diagnoses and possible locations within the heart. If intracardiac catheters 134', 136 or 138 are connected, the process controller 190 can then prompt the user to initiate mode C: Intracardiac Diagnosis and Arrhythmia Localization. This interactive mode will quantify entrainment with concealed fusion to help the physician confirm the diagnosis and location of the arrhythmia circuit. Upon completion of Mode C, the user can then be prompted to enter Mode D: Catheter Guidance to help direct the catheter to an appropriate ablation site. Upon completion of this mode, the user may then be prompted to return to the mode menu. In the illustrated embodiment, the user can terminate any mode manually if desired. Modes C and D can be further enhanced if the ROVE catheter is connected to an intracardiac mapping system (such as by Endocardial Solutions, Inc., or Biosense Webster, Inc.). After ablation, the process controller 190 can suggest the use of mode E: Determination of Ablation Success, or, as with any of the modes, the user can enter mode E directly from the mode menu 220. Upon direct entry into a mode, if the required information has not yet been obtained, the user can be prompted to enter or designate a source for such information. As an alternative example, if the patient starts in a regular rhythm, the process controller 190 will offer the option of enabling mode F: Arrhythmia Prediction, or of inducing the cardiac event by pacing from module 160.

MODES OF OPERATION

Figure 4:
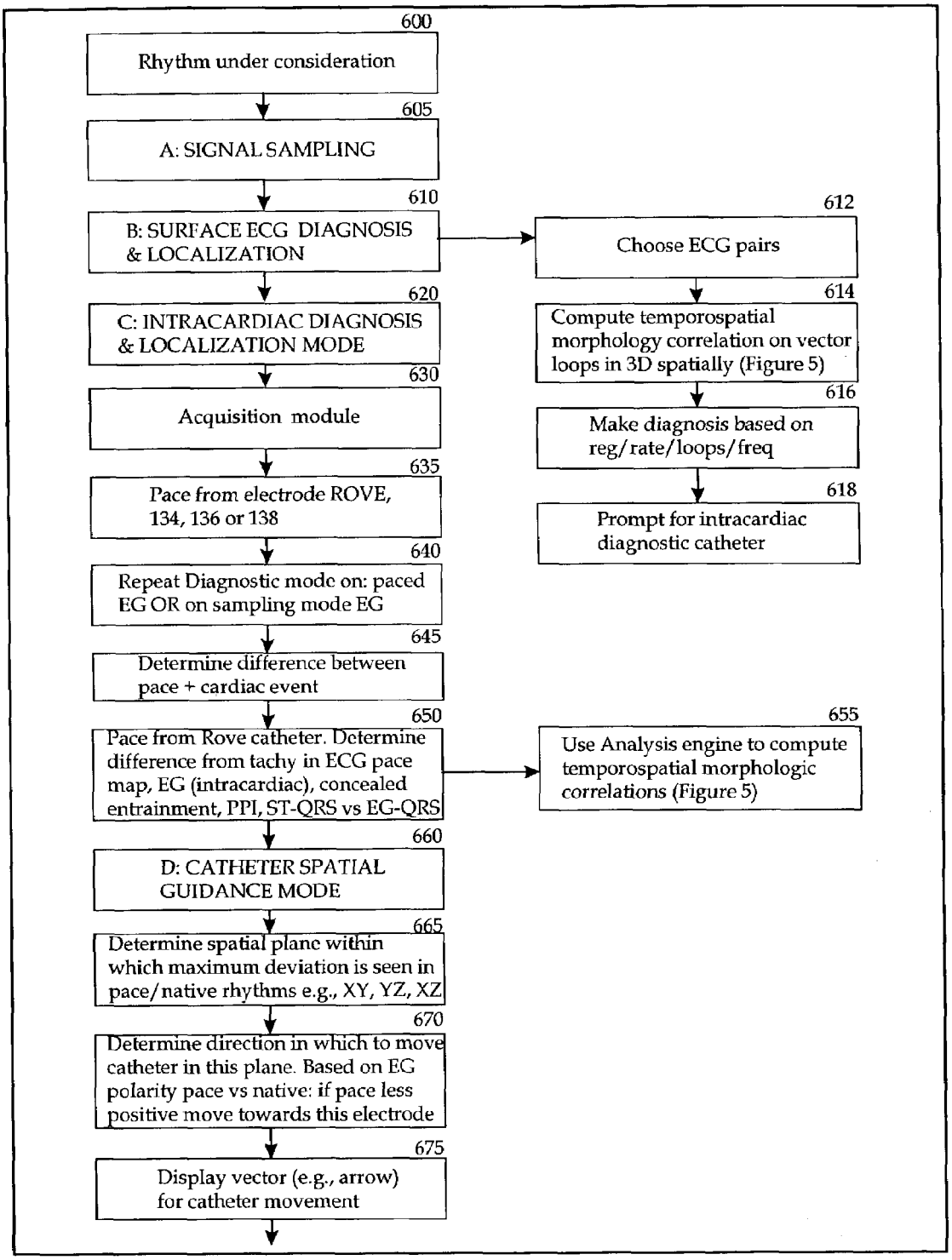
FIG. 4 is a chart integrating modes of operation in accordance with the present invention.
Figure 5:
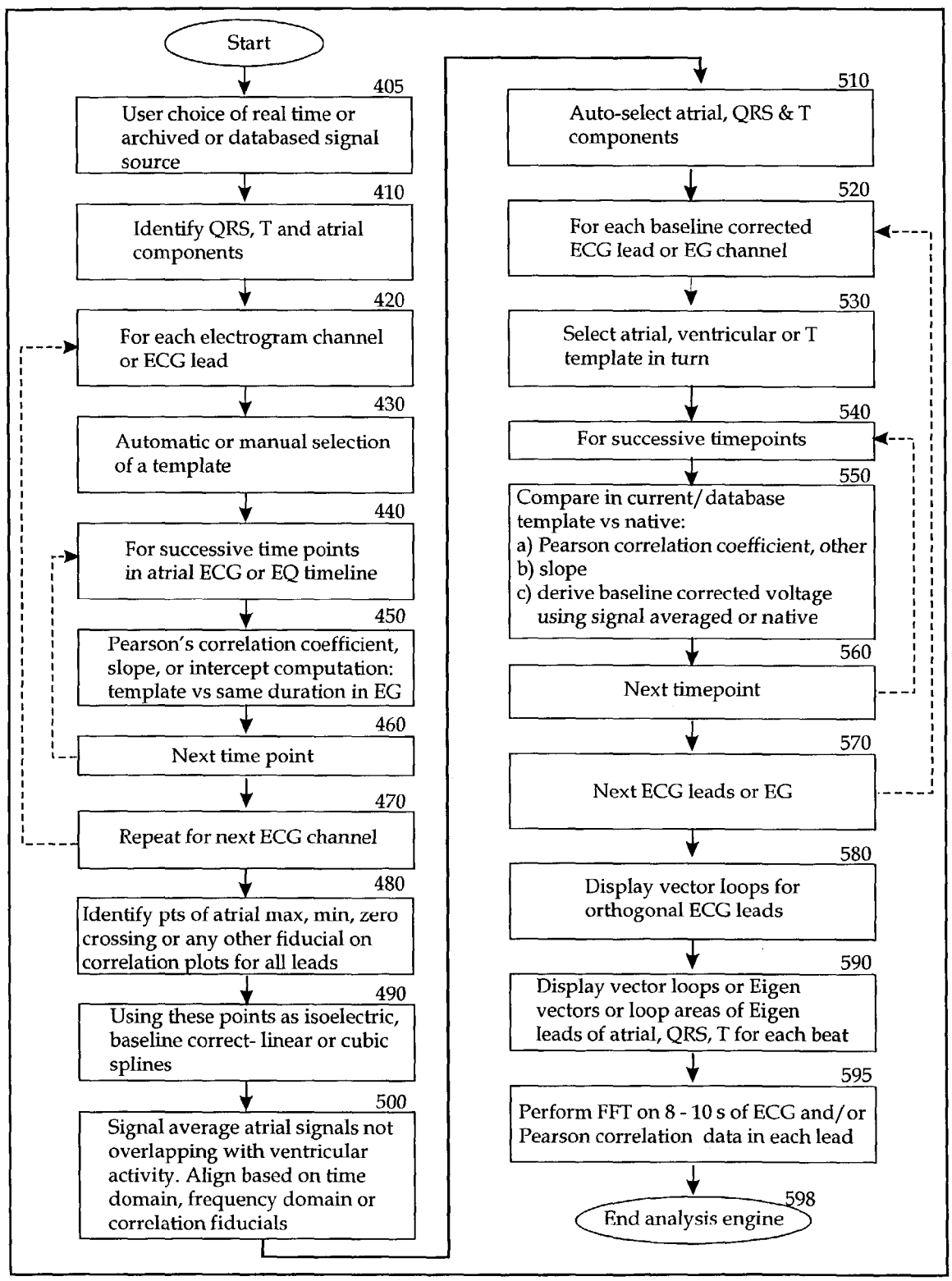
FIG. 5 is a flowchart of an analysis engine in accordance with the present invention.

As previously mentioned, the display 230 shows a menu of six user-selectable modes of operation 220. FIG. 4 provides an overview of the six modes (corresponding to the below headings A–F) of operation of the invention in the preferred embodiment. FIG. 5 expands upon process blocks 614, 655 and 720 of FIG. 4.

A. Signal Sampling

In the illustrated and preferred embodiment, Signal Sampling is performed during an arrhythmia that the physician seeks to diagnose or treat, for example, ventricular tachycardia (VT), atrial tachycardia (AT), atrial flutter (AFL) or atrial fibrillation (AF). This is shown in FIG. 4, process 605. The invention requires digital ECG and electrogram data. However, in cases where these cannot be provided directly, analog sources of these signals can be digitized prior to processing by the invention. In a preferred embodiment, the ECG or electrogram data should comprise at least one cardiac cycle (which generally represents a heart beat). In modified circumstances, a cardiac cycle may include at least one instance of portion of the interval between two instances of the rhythm under consideration. This will include portions of atrial and ventricular activity in sinus rhythm, or simply ventricular activity in ventricular tachycardia, for example.

In one embodiment, the signal sampling mode requires that either ECG electrodes are connected to the body surface 130, and/or that other electrodes are connected such as catheters 134' or an ablation catheter 138 or an electrode 136 in the esophagus 120. During sampling, it is important that the various intracardiac electrodes remain stationary relative to the heart 110, and that the surface ECG electrodes 130 are not re-positioned. In an alternative embodiment, signal sampling can be performed without connecting any catheters, by uploading already-stored electrograms from the database 197 to the process controller 190. In a third embodiment, the process controller 190 interfaces to different acquisition systems 198 to upload electrograms. In this embodiment, the sampled signals can be traditional as well as virtual (or computed) electrograms from a mapping system such as that by Endocardial Solutions, Inc. (St. Paul, Minn.). Electrograms are analyzed in an analogous fashion for all embodiments.

To ensure that adequate contact is made in the desired region of the heart 110 with an electrode catheter 134', 136 or 138, the physician may have to move, rotate, curve or straighten the catheter. The degree of contact can be monitored by the process controller 190 in various ways. For example, the process controller 190 can ascertain contact by comparing the amplitude of the sensed signals during the cardiac event to a predetermined threshold. Alternatively, the process controller 190 can condition the pacing module 160 to emit pacing signals through catheters 134', 136 or 138. The process controller 190 conditions the processing module 150 and sensing electrodes 130, 134', 136 or 138 to detect the pacing stimuli or paced electrograms and use their amplitude to ascertain effective contact. As a third alternative, the processing module 190 can also ascertain the desired degree of contact by measuring tissue impedance.

Once the multiple electrode system is properly positioned, the process controller 190 conditions the electrodes 130, 134', 136 or 138, conditioning module 150 and recording module 158 to record electrogram samples during the selected cardiac event at a given gain and paper sweep speed. The processor controller 190 then records and saves electrogram samples in the host processor 195. In an alternative mode of operation, the user uses module 200 to input instructions to upload previously stored electrograms from the database 197. Other acquisition, recording or archival systems can be interfaced 198 from a 12-lead ECG machine, event recorder, Holter monitor or other systems. This invention can use any user selected data sample rate (such as 1 ms sampling, 4 ms sampling and so on). When data is imported from these systems, the data sample rate will be matched to that of the invention using linear and other interpolation methods. Parts of this process can be performed before acquiring any real-time data. All signals are subsequently analyzed in an analogous fashion.

B. Surface ECG Diagnosis and Localization

The Surface ECG Diagnosis and Localization mode uses ECG signals from electrodes 130 in the standard 12-lead or the Frank X,Y,Z configurations, and is summarized in FIG. 4, processes 610 to 618. The algorithms selected from the menu of actions 210 in FIG. 1B can be relatively easily implemented in software by a practitioner skilled in the art, operate relatively quickly and are suitable for real-time as well as off-line analysis. For example, in one implementation of the algorithm in the Labview programming language running under Windows 2000 on a Pentium 3 PC at 1.2 GHz processor speed, analysis of a full ECG took under one second.

FIG. 5 illustrates a flowchart detailing the primary analysis of this invention of temporospatial morphology correlation. This algorithm comprises several computational steps, described below.

1. Temporospatial Morphology Correlation

Temporospatial morphology correlation is the major analysis of the present invention and a significant advance over prior art methods. It involves correlating the electrographic signal shape ("morphology") to a template over time, then assessing these temporal correlations simultaneously in multiple spatial planes (based on the X, Y and Z directions). It is generally performed after baseline correction (processes 420–500). These processes are designed to compute a baseline voltage, even if this is obscured by continuous atrial activity such as in atrial flutter. The processes, which can be useful for example in Eigen vector calculation, and which can be omitted in modified embodiments, will be discussed later.

In FIG. 5, process 520 commences the algorithm, which can be made on electrographic data or derived signals. Process 530 selects an atrial or ventricular template, typically selected for atrial or ventricular rhythms, respectively.

In a preferred embodiment, the physician will initially (e.g., at step 600) focus his or her attention on a region of abnormality on the patient's ECG. This focus will typically be the atrial signal (P-wave) for atrial rhythm problems. For example, the physician may observe abnormalities (e.g., abnormal shape or vector) in the atrial portion of the ECG. The focus can also be the ventricular portion of the ECG reflecting ventricular depolarization (QRS complex) or ventricular repolarization (the T-wave). The physician may then select a template that primarily includes the activity of interest (e.g., F wave in atrial flutter or QRS complex in ventricular tachycardia). In a preferred embodiment, the invention will provide an automatic selection of template that the user may accept. Typically, the template duration is 70–400 milliseconds, but the selection incorporates the duration of electrical activity and the inter-beat interval to shorten the template at faster rates. Templates have no theoretical upper limit on duration, are typically 50–200% of the duration of activity. The duration of activity may span the entire cycle (for example, atrial flutter or monomorphic ventricular tachycardia), or be shorter (for example, focal atrial or ventricular tachycardias) or longer (such as where alternans arises since atrial or ventricular activation exceeds cycle length). As the template lengthens to span more of the cycle or multiple cycles, such as F-waves (a variant of P-waves seen in AFL) or ventricular cycles in VT, analysis will be more specific for reproducibility but less sensitive since it will be less tolerant of variations in shape or rate.

In an alternative mode of operation, the host processor 190 searches for, locates and uploads a previously stored template from the database 197. This mode allows the current event to be compared against a template of a previous rhythm in this or another patient. Indeed, a particular strength of this method, which will be expanded upon later, is that any signal shape can be used to assess correlation, including a generic template unrelated to the ECG channel in question.

Figure 6:
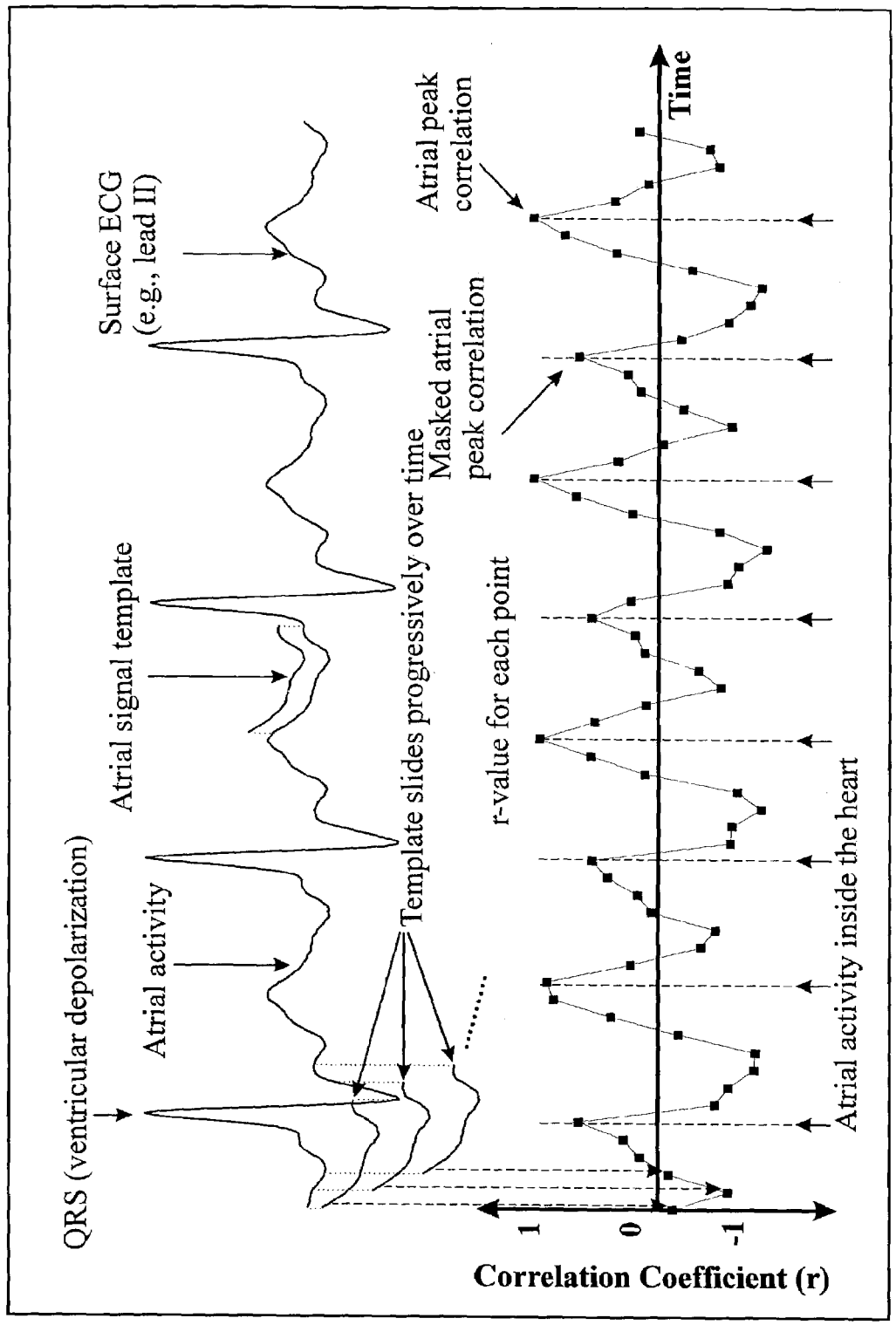
FIG. 6 is a schematic diagram of a method for computing temporal spatial correlation in accordance with the present invention.

FIG. 6 summarizes the main correlation engine for the invention. In a preferred embodiment illustrated in FIG. 6, the ECG signal should comprise at least one cardiac cycle. A cardiac cycle is defined as a heart beat. However, in modified circumstances, it may be defined to encompass a portion of the interval between two instances of the rhythm under consideration. Processes 440, 450 and 460 (and FIG. 6) summarize correlation of the template against a window of the same duration from the ECG. This yields one correlation value. The next correlation is calculated by 'sliding' the template one point (for example, 1 ms) along the digital or digitized ECG. Alternatively, the template can slide more rapidly across the ECG by using steps of 2 or more milliseconds, so that the template is slid more than 1 point per step. The template is then correlated against this ECG. This process is repeated for the entire ECG duration as shown in FIG. 6 (process loop 440 to 460), then repeated for each ECG channel (process loop 420 to 470). Correlation can proceed using Pearson, Fischer or other functions. The preferred embodiment uses the Pearson function, which can be calculated on M pairs of data $\{X_k, Y_m\}$, where $X_k$ and $Y_m$ are samples of fixed duration from the original ECG sequence, as follows:

$$r_j = \frac{M\left(\sum_{k,m} X_k Y_m\right) - \sum_k X_k \sum_m Y_m}{\sqrt{\left[M \sum_k X_k^2 - \left(\sum_k X_k\right)^2\right]\left[M \sum_m Y_m^2 - \left(\sum_m Y_m\right)^2\right]}}$$

where the index in $X_k$, $L \leq k \leq L+M-1$; and the index in $Y_m$, $j \leq m \leq j+M-1$;

$j=1, \ldots, Q-M$ (where Q is the last sample point for analysis in the ECG);

and $1 \leq L \leq Q-M$.

Process 460 performs this repetitive correlation for successive timepoints as shown in FIG. 6. This generates a correlation time series, i.e., a mapping of correlation values against time, for this signal (e.g., an ECG signal in one preferred embodiment). FIG. 6 shows analysis for a digitized cardiac signal, derived from the conditioning unit 150. First, in this case of atrial flutter the upper part of the figure shows clearly separate ventricular activity (QRS complexes) and intervening segments, which include atrial activity and ventricular repolarization (T-waves). These latter two components are difficult to separate visually. An atrial signal template is selected (and labeled) just prior to a QRS complex, to reduce the inclusion of T-wave activity. The invention cross-correlates this template to the original ECG at progressive timepoints, as indicated, generating a series of correlation ("$r_j$") values. The lower part of the figure plots these correlations across time. Periodic r-values oscillate with atrial (and ventricular) cycles over time, reflecting each atrial cycle (correlations approach 1) and superimposition of a QRS complex on alternate atrial cycles (reducing maximum correlation to approximately 0.7). The largest positive excursion of the correlation function is therefore close to 1.0, and the largest negative excursion approaches −1.0.

In general, a "feature" can be identified whenever correlation values exceed a predetermined threshold. A "feature" may comprise atrial depolarization (the P-wave) or repolarization, or ventricular depolarization (QRS complex) or repolarization (the T-wave). In FIG. 6, the clearly evident P-waves (or F-waves of atrial flutter) are identified by correlation values (labeled "atrial peak correlations"). In addition, FIG. 6 also illustrates a "feature extraction" aspect of the invention, wherein atrial activity that is masked by ventricular activity, and therefore not clearly evident in the ECG, is also unmasked by the correlation method. These unmasked P-waves are labeled "masked atrial peak correlations" and overlap with a QRS complex or T wave. Both the "atrial peak correlations" and "masked atrial peak correlations" occur at precisely the same time as signals measured from inside the atria of the heart (depicted by the vertical lines and arrows labeled "atrial activity inside the heart" in FIG. 6, e.g., using a catheter inside the heart). The use of temporospatial correlation frequencies, as described below, can further enhance this function in other cases. The present example illustrates the strength of feature extraction in this invention. This represents a significant improvement over the prior art and is also of benefit in identifying atrial activity for baseline correction as will be discussed later.

Figure 7A:
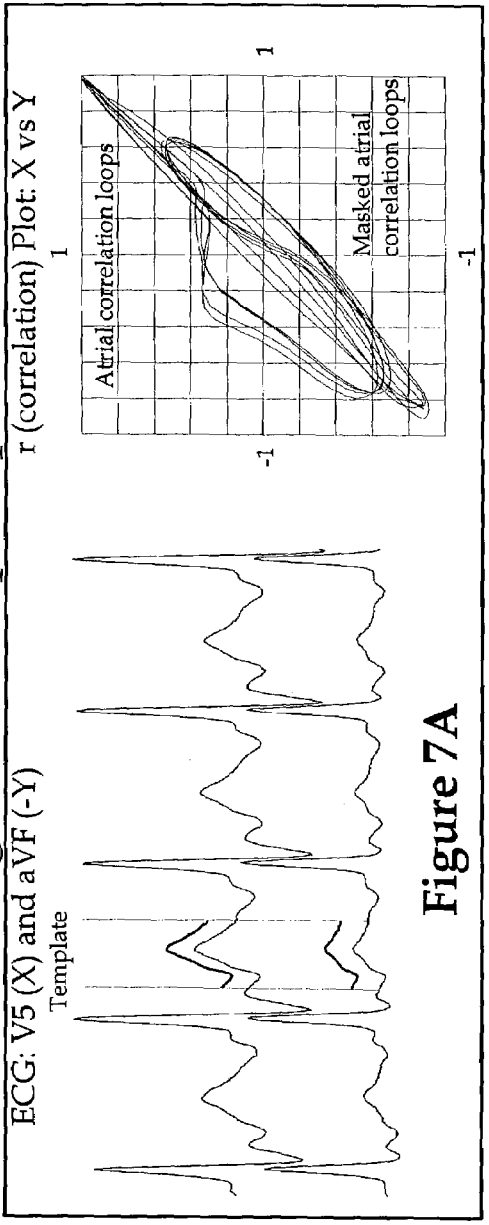
FIG. 7 is a schematic diagram comparing prior-art vectorcardiography with the invention.
Figure 7B:
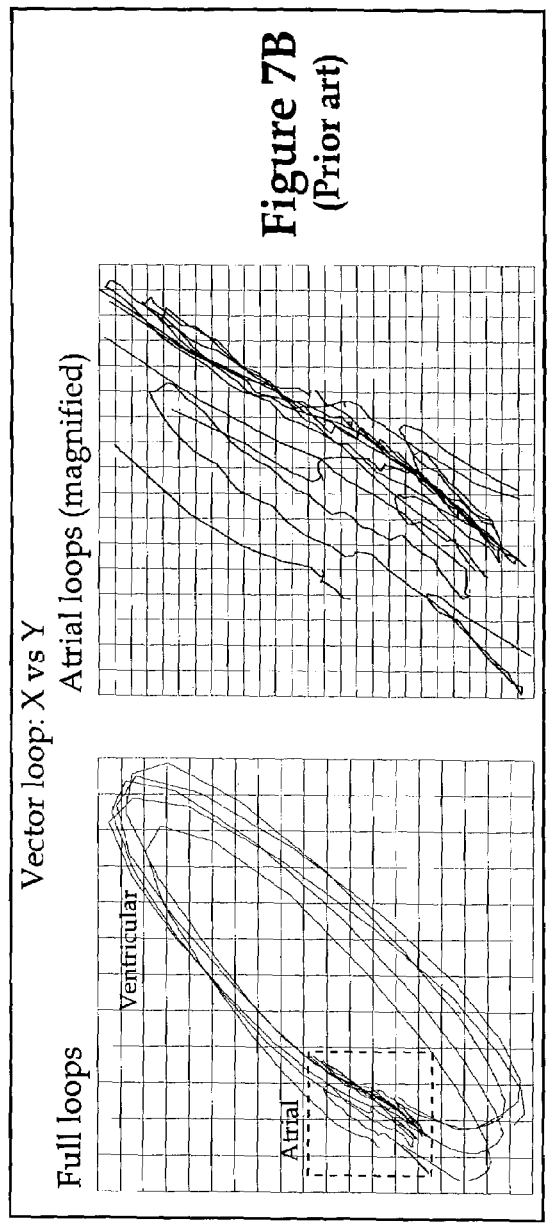

Temporospatial correlation also offers significant advantages over vectorcardiograms (VCG). In the prior art VCG of atrial flutter in FIG. 7B, although the ventricular loops are large their similarity to each other is blurred by small voltage fluctuations from gain and noise effects. Furthermore, the regularity of atrial loops is completely lost in this way, since similar levels of noise overwhelm the smaller atrial signals. This remains even when the VCG is magnified over the atrial portion (FIG. 7B). The temporospatial correlation plot is shown for comparison in FIG. 7A.

Process loop 520 to 570 in FIG. 5 repeats the above correlation analysis for each ECG lead. This generates a correlation time series, i.e., a mapping of correlation values against time, for each ECG lead. Process loop 540 to 560 repeats temporal correlation analysis for successive timepoints, in an analogous fashion to process loop 440 to 460. Process 550 uses separate templates for atrial activity, ventricular depolarization and repolarization. The preferred embodiment computes Pearson correlation, although Fischer or other coefficients can be used.

Process 580 shows temporal correlations plotted for 2 leads to generate a spatial correlation loop for several defined planes (displayed on component 230 in FIG. 1B) using leads V5, aVF and V1 as semi-orthogonal leads X, Y and Z. By way of example, FIGS. 8A–F show the resulting temporospatial correlation loops. A digitized cardiac signal is shown in panel 1 of FIGS. 8A–F. This digitized cardiac signal is represented by ECG leads V5, aVF and V1. Panel 2 shows correlation time series, i.e., mappings of correlation values against time, for each ECG lead. Panel 3 shows the plots of these temporal time series for one lead against another. Specifically, plots are shown for lead V5 versus aVF (XY plane), lead aVF versus V1 (YZ) and lead V5 versus V1 (XZ). Frank orthogonal X, Y, Z leads, or other leads, could be used just as easily.

Figure 8A:
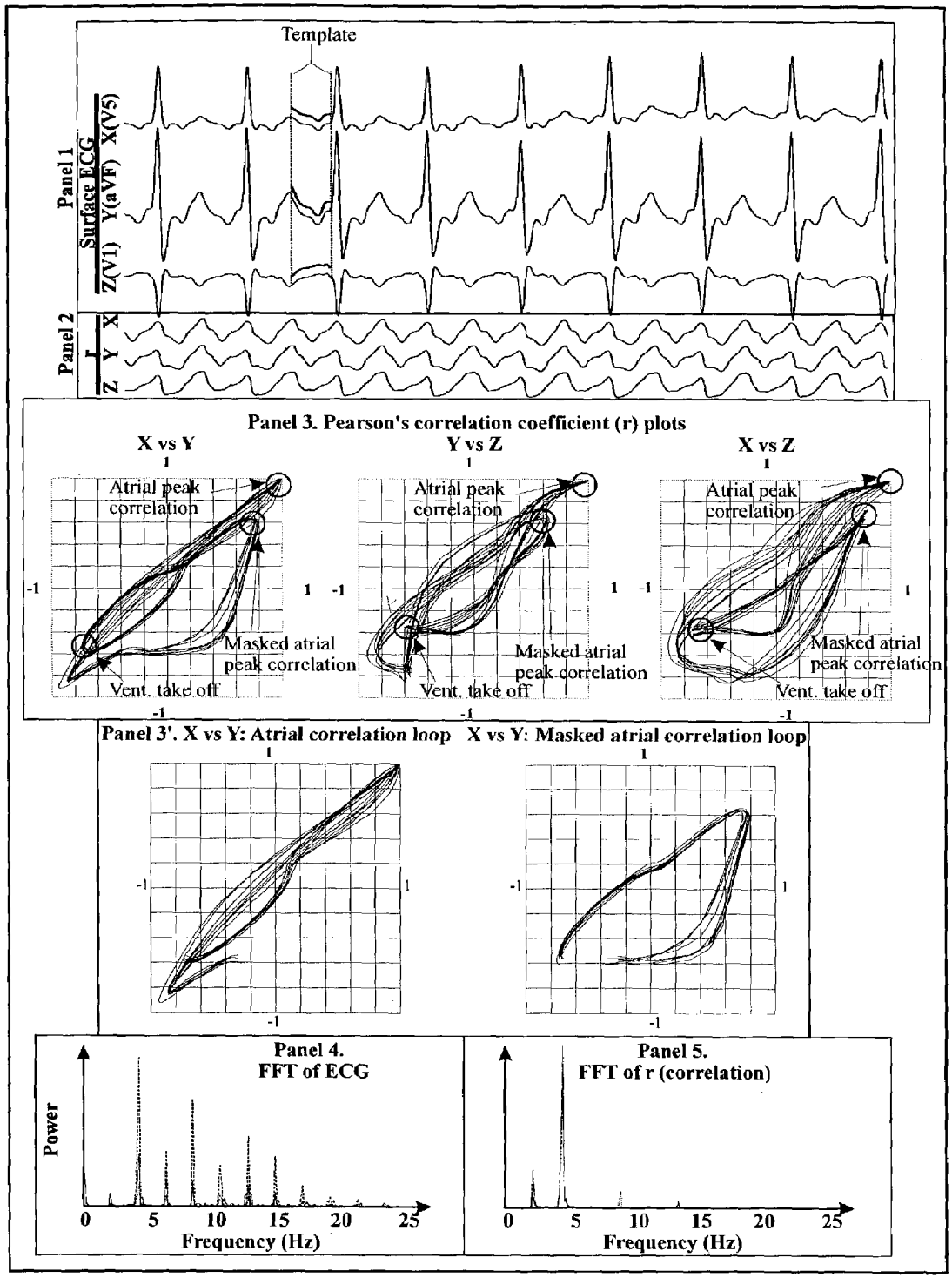
FIG. 8A is a schematic diagram of the invention diagnosing typical atrial flutter.

The distinct atrial and ventricular correlations (in panel 2 of FIG. 8A) give rise to separate loops (FIG. 6 and panel 3, FIG. 8A). First, atrial correlation loops, labeled in panel 3 FIG. 8A, reflect correlations of the atrial template to the atrial portion of the ECG over time. "Atrial correlation loops," generated from successive cycles of atrial activity, are labeled in panel 3' of FIG. 8A. Each atrial correlation loop reaches the (1,1) coordinate (labeled 'atrial peak correlation') signifying that the ECG closely correlates to the atrial template at this time. Each atrial loop also lies roughly parallel to the identity line joining (1,1) with (−1,−1), signifying that activity remains in-phase along each axis of this plane over time. Second, when atrial activity is masked by ventricular activity, the temporospatial correlation method is still able to extract atrial activity and generate loops reflecting this ventricular influence. "Masked atrial correlation loop" indicates these loops in panel 3', FIG. 8A. Since these loops reflect correlations influenced by ventricular activity, they approach but do not reach the (1,1) correlation, at which point they are labeled "masked atrial peak correlations" in FIG. 6 and panel 3, FIG. 8A. The points where atrial correlation loops and masked atrial correlation loops join are labeled 'vent. take off' in panel 3 of FIG. 8A. By analogy, using a ventricular template would result in "ventricular" and "masked ventricular correlation" loops (not shown). In the illustrated embodiment used to generate FIGS. 6 and 8, template duration was 80–200 ms, and the data sampling rate was every 4 ms. However, the number of sampled data points and the data sampling frequency can be varied by the user.

Other applications of this method will be described later. For example, in Mode F: Arrhythmia Prediction described later, temporospatial correlation can measure alternans of the P-wave, QRS complex or the T-wave. In these cases the invention will determine the slope and intercept of the best-fit line joining all of the correlation points. Parameters of these lines such as their variability, or dispersion, patterns of alternans and abrupt changes or discontinuities, may indicate patterns of alternation or alternans between successive cycles.

2. Rationale for Temporospatial Correlation

The current invention exploits the concept that regular activation within the heart will produce repeatable electrical wavefronts on the surface ECG. These wavefronts should retain a consistent relationship between each spatial axis, or remain spatially in-phase, and should be reproducible between successive cycles. Variable activation wavefronts, including the "functional reentry" of atypical AFL or AF, will have additional directions of activation and therefore deviate from this temporal and spatial reproducibility. Temporospatial correlation has been designed to exploit this concept.

By way of example, typical (isthmus-dependent) atrial flutter is characterized by a re-entrant activation wave that follows a very reproducible three-dimensional spatial path in the atria. This involves continuous activation in a counter-clockwise or clockwise direction around a region known as the tricuspid annulus in the right atrium. All other atrial regions are activated passively and secondarily. The resulting atrial activation exhibits a "saw-tooth" appearance in the inferior ECG leads (II, III, aVF), with discrete signals in lead V1 (see FIG. 8A panel 1). However, atrial activity is of low amplitude, easily obscured by the T-wave and noise including baseline wander, line frequency noise, respiratory and muscle artifacts, and other sources. It is readily seen, in FIG. 8A, how the QRS and T waves can obscure it. Therefore, the diagnosis of typical AFL from the ECG is often difficult. Although AFL has been described by way of example, this regularity also applies to regular monomorphic VT, while variable activation applies to polymorphic VT or ventricular fibrillation.

Temporospatial correlation is supplemented by additional analyses to improve the diagnostic ability of the invention. First, Eigen vectors are computed in process 590 in FIG. 5, for the correlation timeplots, the original ECG signals and derived Eigen leads. These analyses assess the plane of maximum energy for the correlation plots and the ECG, each of which identifies the plane in which the arrhythmia circuit is most likely to lie. This information is used in Mode D: Catheter Guidance System, described fully later. In process 595, the additional computation of frequency and power spectra for original electrograms and correlation values provides another means for assessing regularity. Notably, since correlations equally weight atrial and ventricular activity, frequency analysis of these signals will identify their relative rates of activation, and de-emphasize the frequencies that contribute to the different shapes and amplitudes of each complex.

3. Advantages of Temporospatial Correlation Analysis

The significant advantages of temporospatial morphology correlation over methods of the prior art are that it assesses several attributes concurrently, in a computationally efficient manner. Referring to FIGS. 6, 7 and 8A–F, the method assesses and provides:

1. Similarity of the ECG event to the template, signified by a cross-correlation approaching 1. The electrogram events are typically complex signals, and their detailed shape is reflected in the morphology cross-correlation analysis. Thus, each atrial or ventricular wavefront will be assessed against its relevant sampled wavefront.

2. Amplification of low-magnitude signals of interest. For example, this allows analysis of atrial activity which is small and therefore very sensitive to noise. Atrial activity is poorly represented during arrhythmias in the traditional method of vectorcardiography, shown for comparison in FIG. 7B.

3. Detection and extraction of superimposed atrial and ventricular activity. Using cross-correlations to selected atrial (or ventricular) activity, the method accurately feature extracts each atrial cycle and its timing during AFL even if superimposed on a QRS complex (see FIG. 6). This method is also very effective in separating distinct activity when superimposed on electrograms recorded from inside the heart.

4. Maintenance of the same spatial activation sequence from cycle to cycle. This is measured by the spatial phase and, when coherent (in-phase), indicates that activation (correlations) are high or low between leads simultaneously for multiple cycles. Such loops of correlations between spatial planes are shown in FIGS. 8A–F, panel 3. First, correlation loops for reproducible activation will approach the correlation coordinate (1,1) per cycle. Second, spatial coherence is seen when the entire loop, or a significant portion of it, lies predominantly parallel to the identity line from (1,1) to (−1,−1). Third, if a template is selected from a different set of ECG data or even another patient (from one of the alternative embodiments described above), correlation loops should still be reproducible yet may no longer follow the line of identity.

5. Spatial reproducibility of activity, such that temporospatial correlation loops (FIG. 8A) are almost superimposable for successive cycles.

6. Variations in rate of the same rhythm—signified by correlations approaching 1 at different times from cycle to cycle (FIGS. 8A–F panel 2), or reproducible loops that have differing periods (durations) across cycles (see FIGS. 8A-C, panels 3).

7. Alterations in the rhythm—signified by a sudden change in the shape of the temporospatial correlation loop at some point in the ECG.

8. Accurate spectral assessment of electrical activity for each chamber. Since temporal correlations are of normalized amplitude, their frequency analysis more accurately assesses the rate of activation than the analysis of raw electrograms, which are influenced by frequencies contributing to the shape of the (largest) QRS component. This is seen clearly by comparing spectra from electrograms (panel 4) and correlations (panel 5) of FIG. 8C of atypical atrial flutter.

Figure 8B:
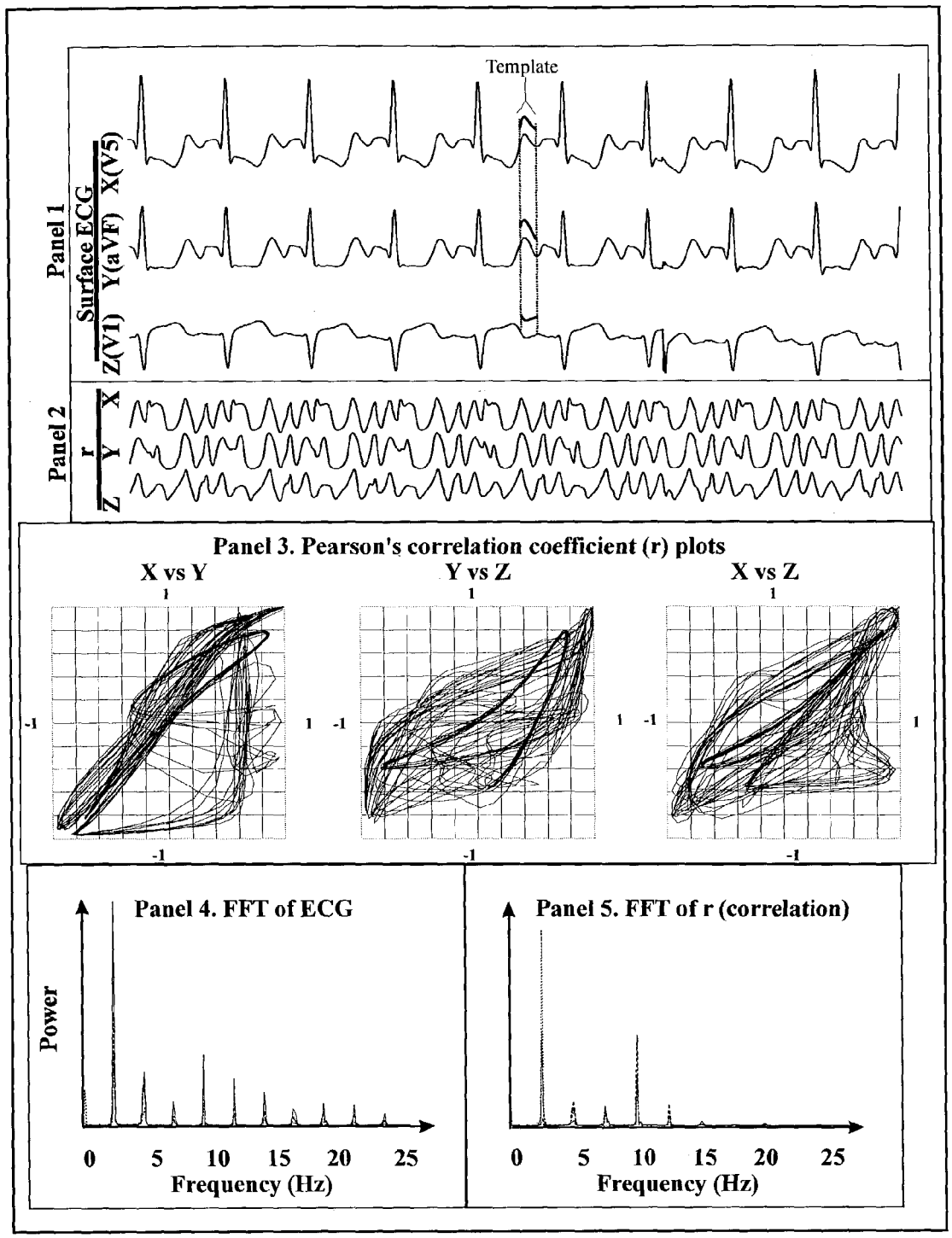
FIG. 8B is schematic of the invention diagnosing atrial tachycardia.

9. Accurate assessment of atrial-to-ventricular relationships, represented by the number of atrial to ventricular loops, and also the time within the atrial loop at which the ventricular loop arises. This analysis identifies whether ventricular and atrial activity are related (as in FIG. 8A), variable (as in FIG. 8C) or independent (FIG. 8F).

10. Detection of isoelectric intervals in the ECG as a clustering of low correlation values centered on zero (0,0). This is seen in sinus rhythm and some atrial tachycardias. Alternatively, a featureless template sample may give rise to extreme correlation values that are unchanging over a period of time. This "temporal invariance" is illustrated in FIG. 8B for a case of atrial tachycardia.

11. Insensitivity of the analysis to factors including baseline wander and electrographic signal gain. This provides a significant advantage of this method over the prior art vectorcardiography. Traditional vector loops (FIG. 7B) are degraded significantly by baseline wander, variable gain and lack of isoelectric definition. The present invention overcomes these shortcomings.

These attributes give extremely high sensitivity and specificity for atrial and ventricular arrhythmias, including their atrioventricular relationships. A major strength of the current invention is that it significantly improves the diagnosis of subtly different arrhythmias, such as typical AFL versus atypical AFL or typical AFL versus combined AFL/AF, from the standard surface ECG. These distinctions can be important since these distinct entities often require quite different therapies.

It must be noted at this point that this analysis also has potential applicability in the field of electrical engineering, such as to assess frequency variability ("jitter") in oscillating waveforms, such as those in analogue circuits. In this application, frequency variations would be manifest as amplitude modulations (below a perfect correlation magnitude of 1.0) from cycle to cycle. These differences may be enhanced for discrimination purposes by the use of linear, logarithmic or other scaling methods.

4. Examples of ECG Diagnosis

FIG. 4 shows a flowchart outlining the modes of operation of the invention. Processes 612 to 618 summarizes the diagnostic part of the invention and illustrates how the algorithm components shown in FIG. 5 and described above work together. In process 612, ECGs are selected for analysis then analyzed for temporospatial correlation and frequency analysis, as mentioned above (process 614), to result in correlation loops for each plane (lead-pair).

The invention can diagnose atrial or ventricular arrhythmias although it is particularly effective for atrial arrhythmias, which are generally more difficult to diagnose since atrial signals have lower signal to noise ratios. Examples will shortly be provided but should not be seen as limiting the applicability of the invention in any way. FIG. 8 shows analysis by the invention for A. Typical isthmus-dependent atrial flutter, B. Focal atrial tachycardia, C. Atypical atrial flutter, D. Atrial fibrillation, E. Monomorphic VT, and F. Polymorphic VT. Each of FIGS. 8A–F has the following components. Panel 1: Orthogonal ECG leads (V5, aVF, V1), with templates illustrated. Panel 2: Correlation values over time for each lead. Panel 3: Temporospatial correlation plots for the planes given by lead pairs V5 and aVF (XY), leads aVF and V1 (YZ), and leads V5 and V1 (XZ). Panels 1, 2 and 3 represent 4 seconds of data. Panel 4: Power spectra for each ECG lead in panel 1. Panel 5: Power spectra for each correlation plot in panel 2. Panels 4 and 5 are computed over 8.2 seconds of data. In each case below, the diagnostic steps are outlined one at a time from the perspective of a human user. However, these components could easily be analyzed using neural networks, or a deterministic or other expert system.

FIG. 6, which has already been discussed above, shows the temporal correlation method for typical atrial flutter. Briefly, processes 510 to 530 (FIG. 5) identify atrial activity and select a template (upper panel; labeled), just prior to a QRS complex to minimize T-wave inclusion. Processes 540 to 560 (FIG. 5) cross-correlates the template to the ECG at successive timepoints to produce plots of correlation (labeled "r-value for each point") against time. A periodicity in r-values is clearly seen, with values approaching 1 for each repetition of the template (clean F-wave), and distinct values when the template slides across the QRS complex. Peak correlations correspond precisely to intra-atrial activity, as shown in the FIG. 6.

Isthmus Dependent (Typical) Atrial Flutter

Now turn to FIG. 8A. This provides, by way of example, the preferred mode of operation analyzing typical isthmus-dependent atrial flutter. This rhythm is characterized by a re-entrant wavefront of activation that follows a very reproducible three-dimensional spatial path in the atrial tissue. This involves continuous counter-clockwise or clockwise activation in the right atrium, parallel to the plane of the tricuspid valve. Left atrial activation then follows secondarily along stereotypical paths involving the coronary sinus musculature and tissue known as "Bachmann's bundle". The resulting atrial activation exhibits a "saw-tooth" appearance in the inferior ECG leads (aVF, II, III), with discrete signals in lead V1. However, these F-waves are of low amplitude, easily obscured by the T-wave and noise such as baseline wander, line frequency noise, respiratory and muscle artifacts, and other sources. Therefore, atypical forms of atrial flutter with different F-waves are often mistaken for typical AFL.

The present specification exploits the temporal and spatial regularity of this activation by determining whether correlations remain in-phase in all spatial dimensions simultaneously. In FIG. 8A, panel 3 shows that the invention compares temporal correlations for pairs of ECG leads defining each spatial plane. Only 4 seconds of data are presented for clarity. In practice, any duration may be analyzed although 8–10 seconds are typical and sufficient. The correlation loops formed by sliding this template across the ECG results in the temporal correlations shown below the ECG (process loop 540 to 560 in FIG. 5).

Repeating this for all ECG leads (FIG. 8A panel 3 and FIG. 5 process loop 520 to 580), results in spatial correlation loops for planes XY (V5 versus aVF; coronal), YZ (aVF versus V1; sagittal) and XZ (V5 versus V1; axial) for simultaneous timepoints. Atrial and ventricular correlation loops are readily identified and are labeled. The point of ventricular takeoff from each atrial loop is also labeled.

It can be seen that atrial (and ventricular) loops are reproducible in each spatial plane. In addition, each atrial loop approaches the (1,1) coordinate and is spatially in-phase {lies roughly parallel to the identity line joining (1,1) with (−1,−1)}. In particular:

1. Panel 2 confirms continuously varying atrial activity, with correlations that vary continuously over time, without a clear isoelectric, which is reflected by a period of unchanging correlations. This finding is more supportive of the diagnosis of atrial flutter than of atrial tachycardia (where isoelectric TP, PR and other segments may be seen).
2. In panel 3, a determination can be made as to whether each atrial peak correlation passes beyond a predetermined threshold coordinate (x, y). When this occurs, it can be determined that the atrial template (in this case the flutter wave) is occurring repeatedly, i.e. at both atrial peak and masked atrial peak correlation points (in FIGS. 6 and 8A). Therein lies the basis for feature extraction in the invention. In a preferred embodiment, x=0.8, y=0.8. This similarity to the original template (wavefront sample) in three dimensions excludes atrial fibrillation and atypical forms of atrial flutter.
3. Panel 3 also shows that the principal axis of atrial correlation loops lie almost parallel to the line of identity. This indicates spatial phase coherence, or that the correlations are simultaneously high or low in each axis.
4. Panel 3 shows reproducibility of successive correlation plots, showing that successive atrial cycles are reproducible over their entire duration.
5. Panel 3 also shows very similar areas of atrial correlation loops. These areas can be computed since the loops are essentially "closed" per cycle. In cases where the loops do not completely close, interpolation methods are used to close the loop and compute areas in three dimensions. Lower variability or dispersion in correlation loop areas from cycle to cycle is a strong indicator of reproducibility in time and space.

Process 590 reduces these indices into a single parameter, a coherence reproducibility index, C, comprising the following assessments:
  (a) The maximum correlation reached in each plane over multiple cycles, represented as loops reaching (x,y). A higher correlation indicating greater reproducibility and, in one preferred embodiment, x=0.8, y=0.8.
  (b) Slope of the principal axis of the correlation loop, relative to the line of identity joining (−1,−1) to (1,1). This is a measurement of spatial phase and, if coherent, tends towards this line of identity.
  (c) Correlation loop variance between successive cycles for each spatial plane; a lower variance indicating greater reproducibility.
  (d) Correlation loop area variance between successive cycles for each spatial plane; a lower variance indicating greater reproducibility.
  C is designed such that a higher value indicates a greater likelihood of a regular, reproducible arrhythmia over time.
6. Panel 3 in this case therefore reveals spatial coherence in all planes. Temporospatial coherence indicates that spatial phase is maintained, i.e. that loops lie parallel to the line of identity (X=Y, Y=Z, X=Z) and have peak correlations that approach (1,1). From the above analysis, coherence reproducibility indices are calculated for each plane. The XY plane (leads V5/aVF) is the most sensitive indicator for atrial flutter (typical or atypical). In this case, if the XY loop is not temporospatially coherent then, pending spectral analysis (described below), another diagnosis is more likely. It should be stated that data from each plane can be condensed into and derived from a single three dimensional plot. However, a series of two dimensional plots is shown for clarity and ease of understanding.

Points 1–6 exclude atrial fibrillation and support the diagnosis of atrial flutter over focal atrial tachycardia.

7. Panel 3 depicts a major strength of the invention—automatic segregation of atrial and ventricular activity. Note that a different correlation loop arises as the atrial template correlates against each QRS complex (labeled "Vent. take off").
8. Note also that ventricular loops are also consistent and reproducible, confirming that ventricular morphology does not change during the recording.
9. Panel 3 therefore also depicts the ability of the invention to feature extract a desired waveform, such as the illustration of atrial and masked atrial activation in FIGS. 6 and 8. Despite the fact that alternate P-waves (or its variant, the F-wave, in atrial flutter) are clearly masked by QRS complexes (see FIG. 8A, panel 1), each atrial cycle is clearly seen (see FIG. 8A panel 3 and 3'). In general, the invention will separate "pure" atrial or ventricular activity from those influenced by the other chamber. As shown in FIG. 6, this allows atrial activity to be consistently detected, and timed precisely with atrial signals from inside the heart, even for P-waves that are buried within the QRS complex.
10. Temporospatial ECG correlation can better extract the timing of intra-cardiac activation, in certain cases, when used in conjunction with correlation spectra. When correlation plots deviate from sinusoidal (that is, they contain a band of discrete frequencies rather than simply one fundamental), frequency decomposition of this band will identify times when the activity under consideration (the F-wave in FIG. 6) occurs. These times correlate well with intra-cardiac signals in these cases.
11. Further, panel 3 shows the relative rates of atrial and ventricular activity. The number and duration of atrial and ventricular loops remains constant throughout the ECG segment, so that the ratio of atrial to ventricular events is fixed.
12. Panel 3 also shows the exact temporal relationship between atrial and ventricular activity, in addition to their ratio. Specifically, each ventricular loop arises from the same point of each atrial loop. This supports a physiologic atrial to ventricular relationship, and weighs against arrhythmias where atrial and ventricular activity are independent but appear associated by chance because of similar rates (known as "iso-rhythmic dissociation").

All of these features point to the most likely diagnosis of atrial flutter with constant A:V conduction, although a focal atrial tachycardia cannot yet be excluded. The invention now uses additional analyses.

Process 590 of the invention computes Eigen vectors and leads to define the spatial plane containing the greatest power content of the ECG. The 2 Eigen vectors of maximum amplitude define the plane and vector resultant containing the maximum power in all 3 ECG leads. Eigen computation first requires the definition of a point of zero power or amplitude. This is the rationale behind the rigorous baseline correction above (processes 420 to 500 in FIG. 5). Eigen vectors are then computed using standard mathematical techniques for each cycle as well as for the entire sequence. An Eigen vector whose orientation does not vary between cycles is another index of a regular and reproducible rhythm; while the converse is true. Similarly, cases in which one Eigen plane encompasses most of the ECG power indicates a regular reproducible rhythm event. Eigen vector analysis can also be focused on ECG regions, such as atrial or ventricular depolarization or repolarization. This alternative embodiment can assess variations in the T-wave, such as T-wave alternans [30], and is computed by excluding ventricular or atrial activity, respectively, from the calculation. Similarly, the 'isoelectric' interval can be defined to essentially threshold 'in' or 'out' the activity of interest.

In the example in FIG. 8A, Eigen vector analysis confirms a temporally and spatially reproducible atrial rhythm. This supports a diagnosis of typical atrial flutter with reentry around the tricuspid annulus or focal atrial tachycardia with activation parallel to this plane. The Eigen vector in this case had minimal variance, indicating little variation in the three dimensional plane of maximum energy between cycles.

Finally, panels 4 and 5 in FIG. 8A show the results of spectral decomposition across the entire (non-segmented) ECG lead and its correlation plot. Several methods can be applied to perform spectral decomposition, including fast and discrete Fourier transformation, wavelet decomposition and other methods. Results from this analysis are usually plotted as power or spectral magnitude (vertically) for several spectral frequencies (horizontally). Power is calculated in the preferred embodiment.

Finally, spectral analysis is performed on the ECG as well as the temporal correlation time series (that is, on panel 1 and panel 2 data). Panel 4 shows the fast Fourier transform (FFT), with a prominent peak at or around 4 Hz and regular harmonics for each lead (plotted in different line styles). Panel 5 shows that the FFT on correlations shows a more dominant 4 Hz peak with attenuated harmonic amplitudes. This work is a significant improvement over the prior art. First, it agrees with work by Stambler et al. [9] who, from intracardiac signals, showed a 4 Hz peak in AFL. Other prior art, such as U.S. Pat. No. 6,064,906 issued to Langberg from the ECG, and U.S. Pat. No. 6,178,347 issued to Olsson using intracardiac signals, showed similar frequency spectra in AF (4 Hz dominant peaks).

Conclusion. The integration of all of the above analyses suggest a diagnosis of typical atrial flutter for the case in FIG. 8A. This was confirmed on further study. Atrial activity is regular, reproducible and spatially in-phase in all three dimensions, and each ventricular cycle arises at a consistent point from preceding atrial activity.

Atrial Tachycardia

FIG. 8B shows another ECG (panel 1) for which temporal correlations show regular periodicity (panel 2). In panel 3, atrial temporospatial correlation loops show phase coherence. That is, they retain spatial phase, since their principal axes lie along the line of identity, indicating that atrial activity is reproducible in each plane, and they are similar to template since they approach the (1,1) coordinate on each cycle. Ventricular correlation loops are also consistent, at a lower rate. Of note, atrial correlation loops show correlations which (for the region illustrated by horizontal lines in FIG. 8B, panel 3) show periods of unchanging correlation over time ("temporal invariance") such as the XY plot (panel 3). This is seen by its near-horizontal (Y=−1) and near-vertical (X=0.6) loops sections, that suggest that the template is being correlated to an isoelectric or unchanging ECG region. Inspecting panel 1 (FIG. 8B) reveals this horizontal ECG section (particularly in the Y lead).

This finding strongly supports a diagnosis of focal atrial tachycardia with such an isoelectric or unchanging ECG region, since atrial activation on the ECG in atrial flutter is continuous, without diastole. Further, correlation plots show a fixed atrio-ventricular ratio and timing relationships, weighing against atrial fibrillation.

Eigenvector analysis showed a reproducible vector of maximum energy, also weighing against AF and supporting the diagnosis of focal atrial tachycardia. Finally, spectral analysis in panels 4 and 5 show regular atrial activity, without a prominent 4 Hz peak but with regular harmonics. Correlation spectra (panel 5) emphasize a narrower range of frequencies at 2.5 and 10 Hz.

Conclusion. These findings suggest the diagnosis of focal atrial tachycardia, at a rate of 150 beats per minute. This was confirmed on further study. The differential diagnosis includes sinus tachycardia, sinus node reentrant tachycardia or focal atrial tachycardia. The mechanism of tachycardia, whether from reentry or abnormal automaticity, and the location of the tachycardia, can be confirmed from mode C: Intracardiac Diagnosis and Arrhythmia Localization, described later.

Non-Isthmus Dependent Atrial Flutter

Figure 8C:
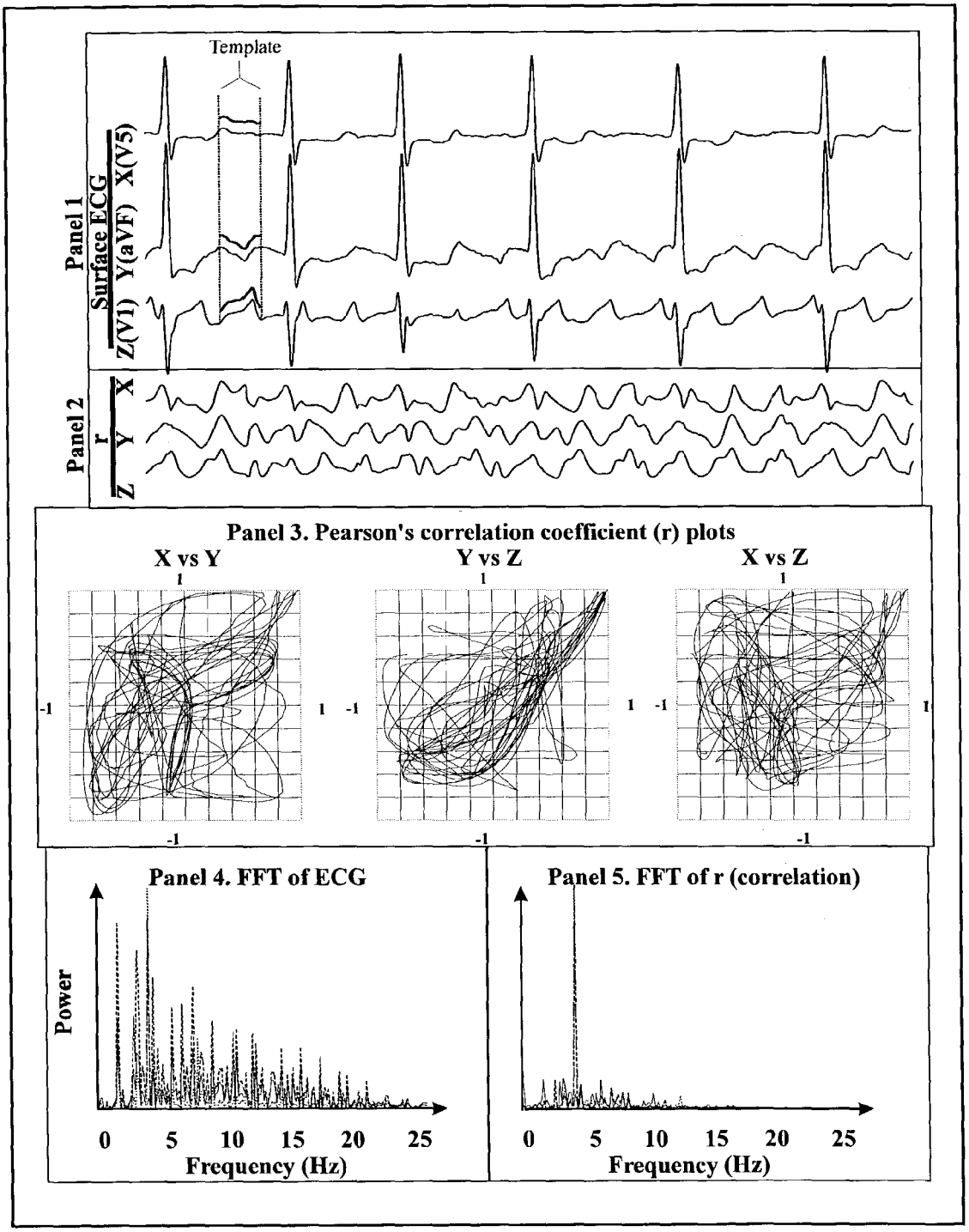
FIG. 8C is a schematic of the invention diagnosing atypical atrial flutter.

FIG. 8C shows another ECG (panel 1), its temporal correlations (panel 2) and temporospatial correlation loops (panel 3). However, several differences are seen compared to the example in FIG. 8A. First, temporal correlations are irregular, despite the somewhat regular ECG appearance, and rarely reach 1. This indicates a lack of similarity to the template (which can be any atrial region) over time. Second, atrial correlation loops (panel 3) are not reproducible in the XY, YZ or XZ planes. This weighs against typical AFL. Furthermore, these loops do not pass the previously described threshold correlation coordinate of (0.8, 0.8), which is consistent with this dissimilarity. Third, ventricular loops have variable take-offs from atrial loops. Fourth, the absence of temporal invariance (described above in the section in atrial tachycardia) weighs against the diagnosis of focal atrial tachycardia.

The diagnosis at this point suggests either atypical atrial flutter or atrial fibrillation. Eigenvector analysis revealed significant variability in the maximum-energy plane between cycles. This is consistent with either an atypical atrial flutter, an organized form of atrial fibrillation or atrial tachycardia from multiple distinct foci. Finally, frequency analysis provides a clue to clinch the final diagnosis. In panel 4, FFT on the ECG showed a broad bandwidth of frequencies. However, by eliminating magnitude differences between atrial and ventricular complexes, and frequencies contributing to their different waveforms, correlation analysis more cleanly assessed true atrial rate. Correlation spectra showed a predominant peak at 4 Hz peak, similar to FIG. 8A. This differs from the broad bandwidth of AF from U.S. Pat. No. 6,064,906 issued to Langberg and U.S. Pat. No. 6,178,347 issued to Olsson.

Conclusions This example shows that this ECG, although consistent with typical AFL, is clearly not typical AFL using the present invention. This was confirmed on further study. Despite the lack of a clear spatial phase relationship, spectral analysis of temporal correlations confirmed one predominant activation rate, consistent with atypical AFL. Atypical AFL sometimes shows spatially coherent loops in the XY plane, while the YZ and XZ planes may be clearly non-coherent. Correlation plots, and spectral analysis on correlation series, are critical to the diagnosis of these arrhythmias.

Atrial Fibrillation

Figure 8D:
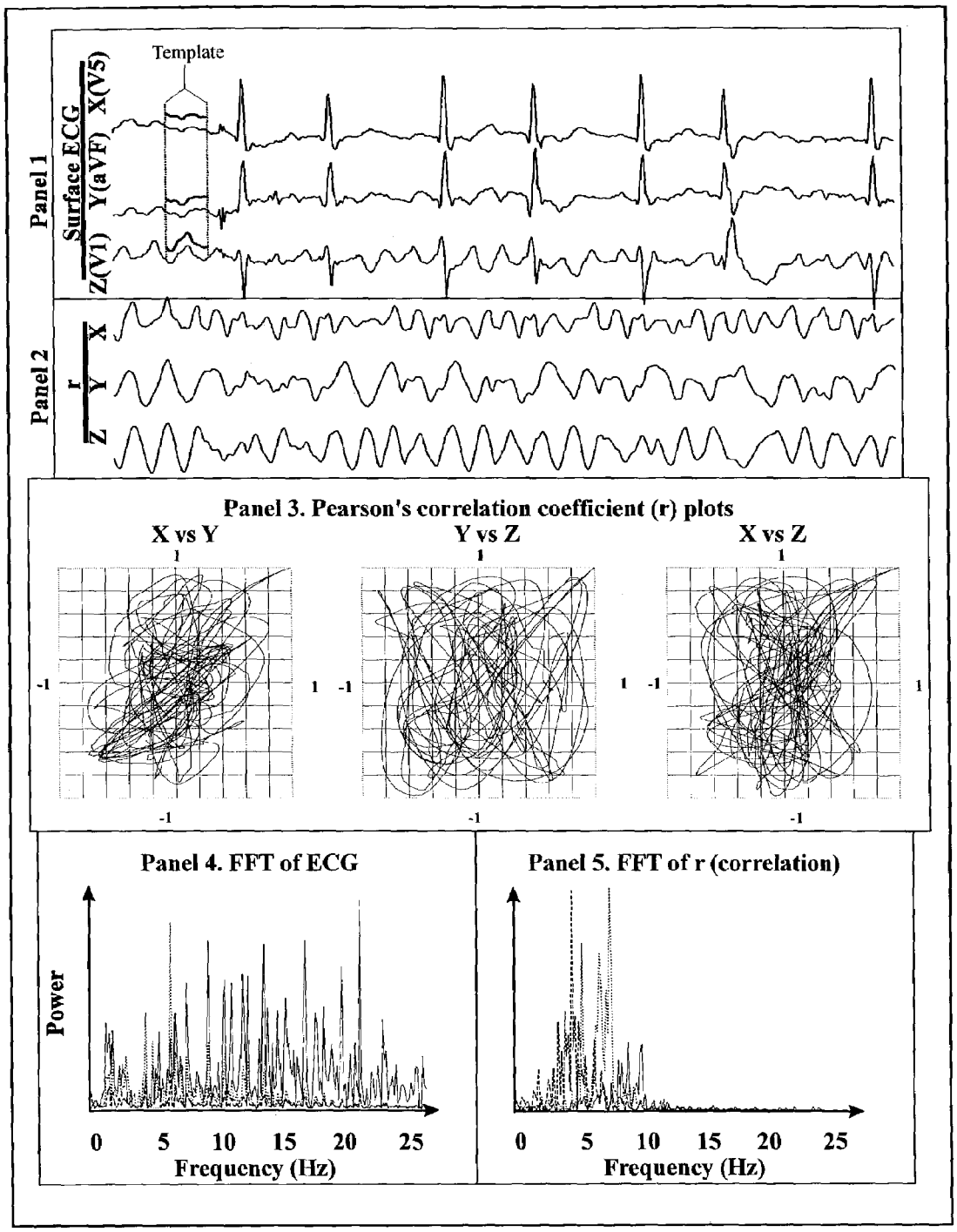
FIG. 8D is a schematic of the invention diagnosing atrial fibrillation.

In FIG. 8D, panel 1 shows irregular atrial activity and panel 2 shows that temporal correlations are not reproducible over time in any lead. Panel 3 shows temporospatial correlation loops that are disorganized and space-filling in all planes. Rather than being reproducible, correlation loops intersect in highly variable directions, reflecting variable spatial activation patterns between cycles in all axes. Furthermore, atrial and ventricular loops have no consistent relationships, and ventricular loops have variable take-offs from atrial loops. These findings suggest an irregular atrial rhythm, such as AF, atypical AFL or focal atrial tachycardia from multiple foci (compare against FIGS. 8A–C).

Eigen vectors in this case showed approximately equal magnitude between axes, without evidence that one plane contained most of the power. This suggests spatial variability in atrial activity and supports the diagnosis of AF. In panel 4, spectral decomposition showed absence of a peak at 4 Hz or consistent harmonics, but rather a broad bandwidth spectrum in all 3 leads. This remains true in panel 5 in correlation spectra, although the bandwidth is narrowed somewhat. From U.S. Pat. No. 6,064,906 issued to Langberg and U.S. Pat. No. 6,178,347 issued to Olsson, although based on intra-cardiac data, this supports the diagnosis of AF.

Conclusions. The combination of irregular and spatially non-uniform atrial activation, with variable atrio-ventricular relationships, confirms the diagnosis of AF. This was confirmed on later study. This pattern is clearly distinct from atypical AFL (FIG. 8C) although traditional prior art methods sometimes cannot distinguish these rhythms.

Monomorphic Ventricular Tachycardia with Atrioventricular Dissociation

Figure 8E:
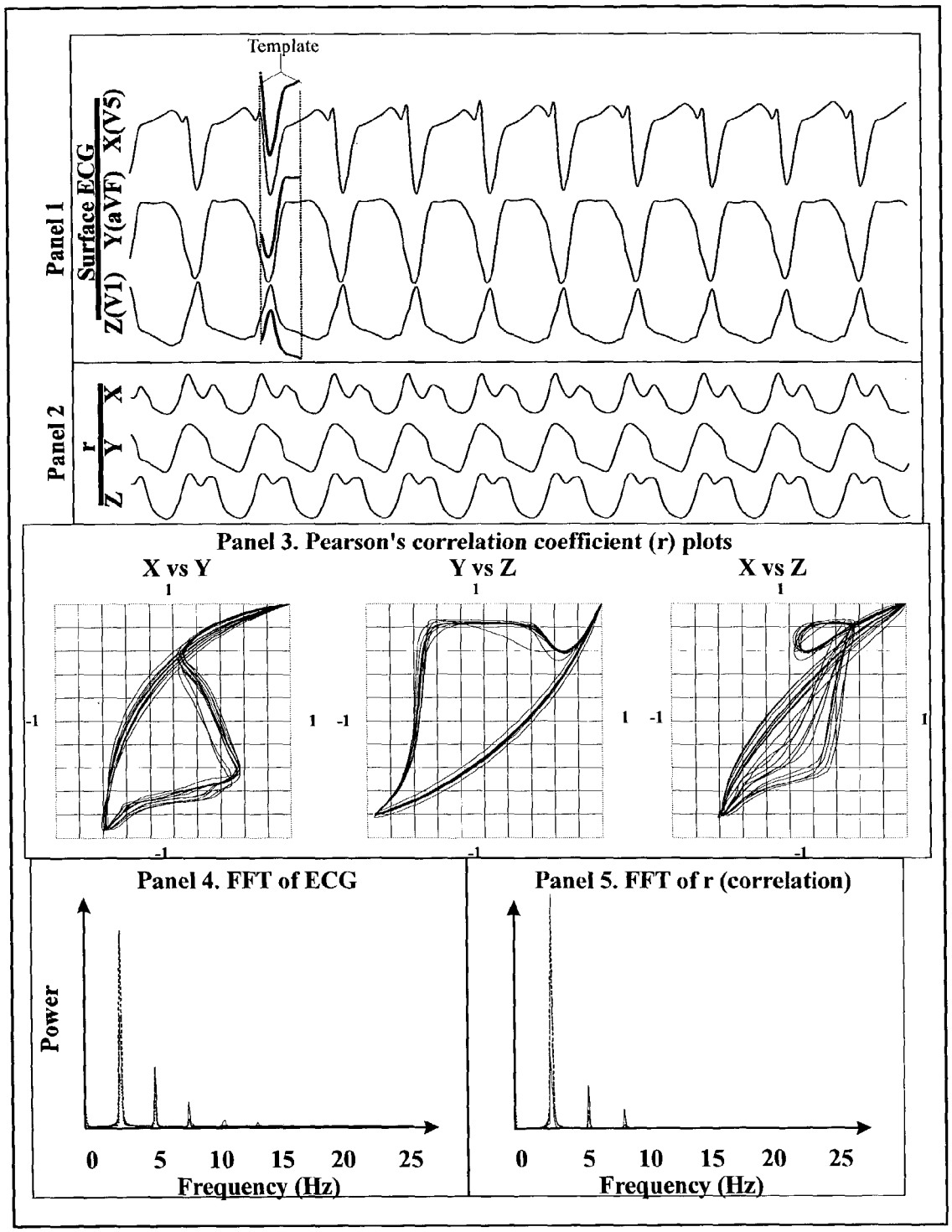
FIG. 8E is a schematic of the invention diagnosing monomorphic ventricular tachycardia.
Figure 8F:
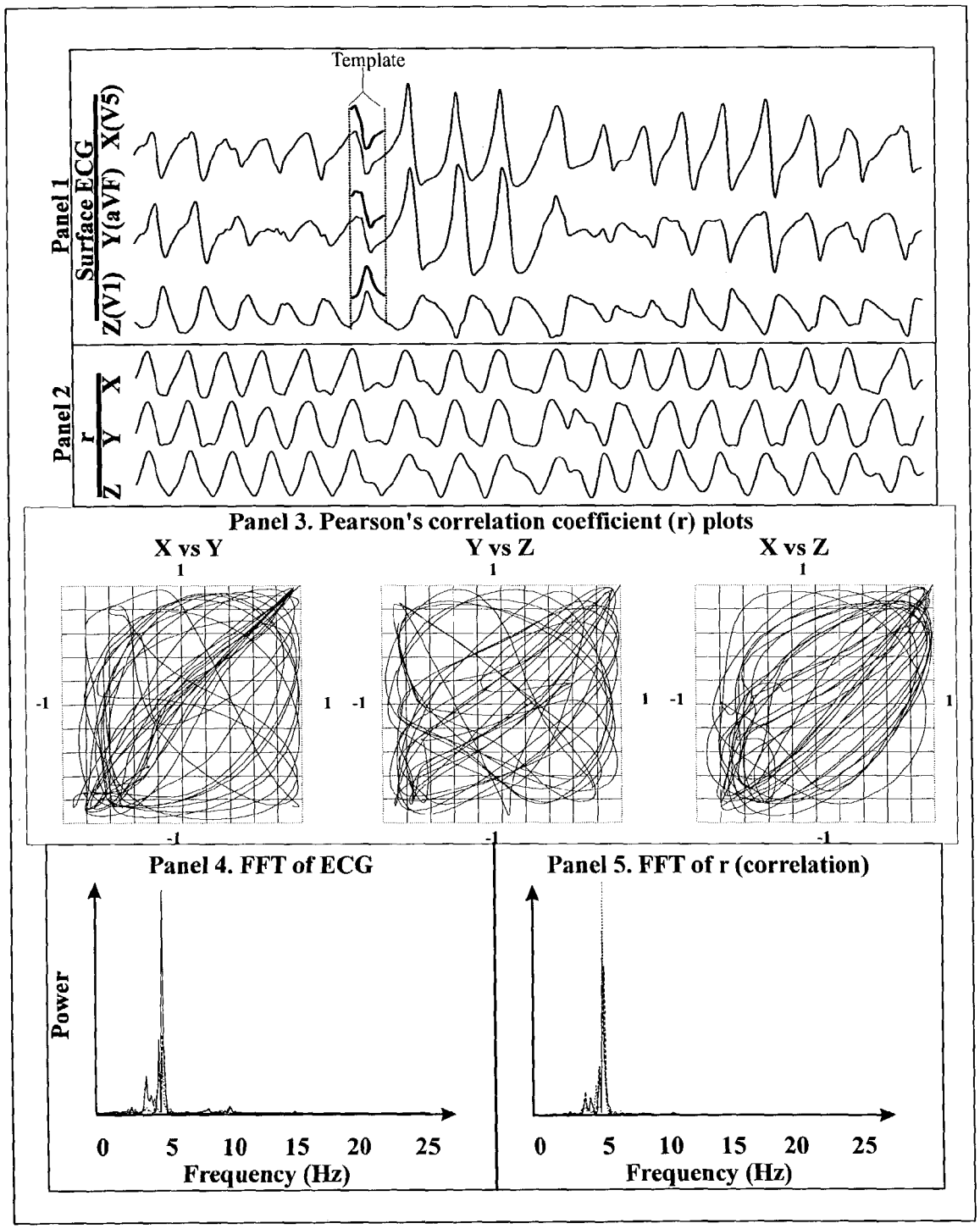
FIG. 8F is a schematic of the invention diagnosing polymorphic ventricular tachycardia.

FIG. 8E, panel 1 shows an ECG of regular wide complex tachycardia. Ventricular activity was used as a template in this case. In panel 2, correlations to this template are regular and periodic, and approach 1.0 for each cycle. In panel 3, activation is reproducible for all cycles. Notably, there is spatial coherence over significant portions of the cycle, shown by those parts of the correlation loop that lie predominantly parallel to the line of identity (1,1) to (−1,−1). Notably, slight variations in the ventricular correlation loops were seen. These corresponded to the presence of dissociated atrial activity seen from intracardiac recordings. Therefore, this analysis was able to discern atrial activity that was not evident on visual inspection of the ECG.

These findings strongly support monomorphic VT. The presence of dissociated atrial activity discounts the possibility of a regular supraventricular tachycardia with wide QRS complexes due to bundle branch block ("SVT with aberrant ventricular conduction"). Eigen vector analysis showed minimal variation in the plane of maximum power, while spectral decomposition, shown in panels 4 and 5, showed regular spectra, each with a clean dominant peak at 2.5 Hz and the absence of non-harmonic frequencies.

Conclusion. These features suggest the diagnosis of monomorphic ventricular tachycardia, which was confirmed. The ability of the method to detect slight correlation irregularities corresponding to atrial activity that is not clearly evident with the naked eye greatly simplifies the diagnosis of VT, which is clinically difficult in many cases [6].

Ventricular Tachycardia with Variable Intracardiac Activation

In FIG. 8F, panel 1 shows an ECG of a very irregular and rapid wide complex tachycardia. In panel 2, analysis of correlations shows that, although they show some reproducibility, they appear to have different phase relative to each lead. This is confirmed by the temporospatial loops in panel 3, which are spatial filling and reach all four vertices of the plot. Correlation lines cross each other in clearly variable directions, as also observed in AF (FIG. 8D). As also seen in AF, Eigen vectors showed that the plane of maximum energy did not contain most of the power. Interestingly, despite tachycardia irregularity on visual inspection, spectra (panels 4 and 5) show a dominant peak at around 5 Hz, with some frequency smearing. There was very little difference between ECG and correlation spectra, supporting that most of the ECG activity arises from either the atria or ventricles.

Conclusion. These results suggest a diagnosis of ventricular fibrillation or polymorphic VT. This was confirmed later, with a rate consistent with the spectral peak. This example also demonstrates that temporospatial correlation (showing lack of temporospatial coherence) clearly adds to the information from spectral analysis (showing one predominant frequency).

5. ECG Comparison Mode

This mode is provided to enable the physician to use the routine 12-lead ECG to determine whether a current rhythm is a recurrence of a previous event, such as atrial flutter after ablation, or a new arrhythmia, such as atypical atrial flutter. This determination is otherwise very difficult using prior art methods. Alternatively, the current arrhythmia can be compared to a previously-stored typical or classic rhythm, such as atrial flutter or right ventricular outflow tract ventricular tachycardia that have stereotypical ECG patterns.

A particular strength of this temporospatial correlation method, that makes this mode possible, is that the template need not be sampled from the ECG being analyzed. The template can actually be any signal shape, or a generic beat, or a template previously sampled from any one of a plurality of potential cardiac events. This is possible since the invention tolerates differences in amplitude scaling, noise and other factors. Previously stored electrograms are uploaded from the database 197 or external interface 198 to the process controller 190, and used as templates for which to compare the current ECG of interest. Electrograms imported in this way have their sample rates matched to that of the ECG of interest using interpolation methods.

Temporospatial correlations will differ somewhat from the above detailed description in this mode when non-ECG sampled templates are used. First, maximal correlations may no longer approach 1.0 if the new template does not match the ECG at any point along its duration. Second, therefore, principal loop axes may no longer lie parallel to the line of identity even in regular rhythms (typical AFL, monomorphic VT). However, such analysis will still produce reproducible loops, and atrial and ventricular components will be readily segregated. Many of the above analyses can still therefore be made.

6. Methods for Computation of Baseline

Baseline correction can be used in the invention, particularly for the calculation of Eigen Vectors. Baseline correction is traditionally performed in the PR or TP segments (where cardiac activity is minimal). However, several rhythms do not show this clear isoelectric segment, such as the continuous atrial activity of atrial flutter. The invention includes a novel method for calculating baseline in these circumstances, using temporospatial correlation as described above.

FIG. 5 process 405 offers the user a choice of considering real-time, previously stored or archived data, or a combination thereof. Process 410 can identify from the ECG components representing ventricular depolarization (QRS complex), ventricular repolarization (T wave) and atrial activity. This may be based on actual ECGs (real-time or stored) or on a derived ECG such as a vector resultant lead. QRS complexes can be identified using methods discussed by Watanabe et al. [25], U.S. Pat. No. 4,552,154 issued to Hartlaub, and U.S. Pat. No. 6,035,231 issued to Sornmo. QRS complexes can then aligned using one of several columnar techniques, including alignment about the point of largest positive or negative slope, peak values, minimum mean square differences, or metrics based on derived signals. T-waves are then similarly identified and aligned, and atrial activity lies in the intervening intervals.

First, atrial and ventricular activity are defined in processes 480, 490 and 500, from the points where correlation to an atrial template approaches 1. Process 480 identifies points of maximum or minimum atrial correlation, zero crossings or other fiducial points. Process 490 computes a linear or non-linear baseline signal through these fiducials using the methods of cubic spline, linear interpolation or other methods. This baseline is then subtracted from each ECG lead to produce a wander-corrected ECG. Process 500 then computes an average signal offset, by aligning atrial cycles. This alignment can be accomplished by time and frequency domain methods or the fiducial points of reproducible correlation values (maxima, minima, zero or other values). The signal offset is the average between the maximum and minimum amplitude points of the atrial signal. This offset is subtracted from each wander-corrected ECG lead to yield the final baseline-corrected ECG. This process may be repeated iteratively to remove baseline artifact.

This method is a significant improvement over prior art methods of baseline correction, such as U.S. Pat. No. 6,035,231 issued to Sornmo. These methods assume that a segment, generally the TP or PR interval, is isoelectric, and subtract it from the ECG. This also helps in reducing T-wave artifacts. Unfortunately, this introduces significant errors in arrhythmias such as AFL, where the isoelectric interval is absent, and when atrial and QRS activity have variable timing. The current invention enables baseline correction even during AFL and other atrial arrhythmias. However, various other methods for baseline correction known to those skilled in the art of ECG signal processing, such as isoelectric subtraction with or without P wave alignment and averaging, can also be incorporated, in addition to or as an alternative to the above-described temporospatial correlation based methods.

C. Intracardiac Diagnosis and Arrhythmia Localization

An overview of this mode of operation of the invention is provided in FIG. 4 commencing at process 620. As can be seen, this mode of operation follows and complements mode B: Surface ECG Diagnosis and Localization in the preferred embodiment. It is then followed, in turn, by mode C: Intracardiac Diagnosis and Arrhythmia Localization.

1. Background for Arrhythmia Localization

Figure 9:
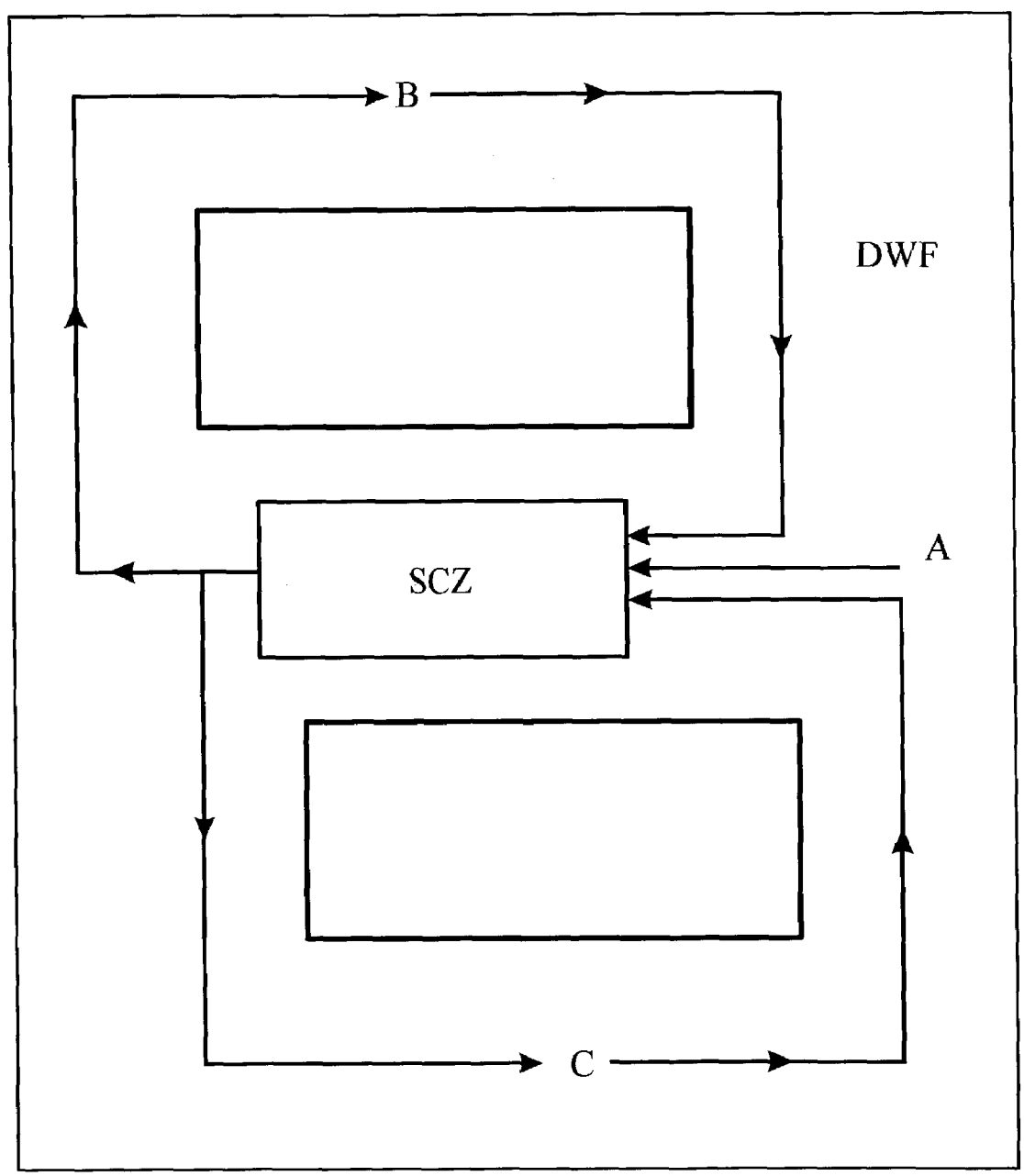
FIG. 9 is a schematic explaining reentry arrhythmias.

By way of overall explanation for a re-entrant arrhythmia, such as VT or AFL, the site most appropriate for ablation typically constitutes a slow conduction zone, labeled SCZ in FIG. 9. Depolarization wave fronts A (designated DWF in FIG. 9) entering the slow conduction zone SCZ (site A in FIG. 9) break into errant, circular propagation patterns (designated B and C in FIG. 9), called "circus motion." Circus motion disrupts the normal pattern of depolarization, and therefore disrupts the normal contraction of heart tissue to cause the cardiac event.

The event-specific ECG and intracardiac electrode samples labeled $S_i$ (i=1 to 3, although of course greater or fewer can be recorded) in FIG. 1B record these depolarization patterns. If a pacing signal is applied at the site of SCZ, the pacing signal gets caught in the same circus motion (i.e., paths B and C in FIG. 9) that triggers the targeted cardiac event. Therefore, many of the pacing morphologies $P_i$ at the sensing electrodes (where i=1 to 3 in FIG. 1B, although of course greater or fewer can be recorded) will be similar to event-specific samples $S_i$. This will result in a high temporospatial correlation (that is, coherence) when using a paced template against the event-specific ECG, or vice versa, using the methods outlined above.

However, if a pacing signal is applied outside an SCZ, the pacing signal is not caught in the same circus motion. It propagates free of circus motion and creates a significantly different propagation pattern than that recorded during the event-specific samples $S_i$. The pacing morphologies $P_i$ at the sensing electrodes will therefore have quite different temporospatial correlations than the event-specific samples $S_i$. This leads to smaller overall correlation, the absence of coherence and different (but potentially reproducible) patterns in each lead-pair plane.

Therefore, the coherence reproducibility metrics have been designed to increase in value when the pacing electrode ROVE is closer to the SCZ, which is a potential site for ablation. Differences in surface propagation when pacing inside as opposed to outside a SCZ are most pronounced during concealed entrainment pacing. For this reason, the invention has been designed to employ concealed entrainment pacing. Of note, any electrode can be used for pacing and recording $S_i$ and $P_i$, but in the preferred embodiment the ROVE catheter is used for this purpose (as shown in FIG. 1B).

2. Acquisition Module

This module is activated first, as shown in FIG. 4 process 630. The process controller 190 records intracardiac and ECG signals during a cardiac event. This is analogous to mode A. Signal Sampling for ECG signals, above. In this module, electrodes on the body surface 130 must not be repositioned, while those elsewhere 134', 136, 138 must remain in a fixed location relative to the heart 110 and its vasculature 114. In the illustrated and preferred embodiment, the cardiac event comprises an arrhythmia that the physician seeks to treat, for example, ventricular tachycardia (VT), atrial tachycardia (AT), atrial flutter (AFL) or atrial fibrillation (AF).

The process controller 190 in this module processes a selected number of electrogram samples obtained from each electrode during the known cardiac event. These event-specific electrogram samples (designated for the purpose of illustration in FIG. 1B as $S_1$ to $S_3$) may be recorded unipolar (between electrode 134', 136 or 138 on the heart 110 or its vasculature 114, and a reference electrode, not shown) or bipolar (between electrodes on each multielectrode catheter 134', 136 or 138 on the heart 110 or its vasculature 114). Bipolar signals may be recorded from specialized catheters such as those recording monophasic action potentials (EP Technologies, Sunnyvale, Calif.), which resemble extracellular action potentials. The samples $S_1$ to $S_3$ can also comprise one heart beat or a specified number of beats. Multiple beats may be averaged to reduce noise, if desired.

The host processor 195 stores the set of event-specific electrogram samples $S_1$ to $S_3$ in memory. The process controller 190 can, for an individual patient, retain sets of event-specific samples for different cardiac events. For example, a patient may undergo different episodes of VT, each with a different morphology. The host processor 195 can automatically detect different VT morphologies and store samples of each episode for analysis. The process controller 190 can also download the samples to the database 197 for off-line analysis at a subsequent time.

3. Pacing Module

In the preferred embodiment, the Pacing Module (FIG. 4, box 635) follows the acquisition module, and must be performed without moving electrodes 130, 134', 136, 138, which must occupy the same positions as they did during the Acquisition Module. The process controller 190 conditions the pacing module 160 to pace the heart 110 in a user-programmable fashion while conditioning the signal processing modules 150 and 158 to record a number of the resulting electrograms. Pacing (or stimulating) the heart results in a paced cardiac signal, which may represented by several ECG leads.

The pacing signal induces depolarization, emanating at the pacing ROVE electrode. Of course, pacing can be applied to any electrode, but in the preferred embodiment this is the ROVE catheter. The process controller 190 processes the resulting paced electrogram samples sensed at each electrode (any combination of 130, 134', 136 138 deployed in FIG. 1B) during pacing. The paced electrogram samples are designated $P_1$ to $P_3$ in FIG. 1B.

Different conventional pacing techniques, including burst pacing and multiple extrastimuli, can be used to obtain the paced samples $P_1$ to $P_3$. Regardless of the particular pacing technique used, the pacing stimulus may be monophasic, biphasic, or triphasic. The paced morphology $P_1$ to $P_3$ at each electrode can be from one heart beat or a specified number of heart beats. The length of the morphologies $P_1$ to $P_3$ can have any relationship to the length of the event-specific samples $S_1$ to $S_3$ for the same electrodes obtained during the acquisition module. Typically, they are of equal duration.

The pacing module can be performed in two preferred modes of operation:

(a) to pace the heart without inducing the cardiac event of interest (the Pace-Map module); or, (b) to pace the heart during the cardiac event of interest without altering this event (the Concealed Entrainment module).

4. Pace-Map Module

The pace-map module is used at a time when the patient is not experiencing the cardiac event of interest. The goal is to compare ECG (and/or electrogram signals) resulting from pacing to those from the cardiac event of interest (recorded previously in the Acquisition Module, uploaded from the database 197 or imported from the interface 198). These signals will become more similar as the ROVE catheter moves closer to the arrhythmia circuit (see Background above and FIG. 9).

Pacing stimuli are applied from the ROVE catheter placed within the heart 110 or its vasculature 114. In a preferred embodiment, this is the ablation catheter 138, but pacing can also be applied at electrodes 130, 134', 136. Pacing is applied at a rate close to that of the cardiac event of interest, but it can be important that the arrhythmia not be induced. The electrodes 130, 134', 136 and 138 must not change their position relative to the heart 110 throughout this module.

In FIG. 4 process 640, temporospatial correlation analysis is repeated using a current template during pacing on a previously stored example of the cardiac event of interest. This is analogous to ECG comparisons in mode B: Surface ECG Diagnosis and Localization mode. First, the process controller 190 selects a template from the ECG and electrogram samples $P_1$ to $P_3$ during pacing. In an alternative embodiment, $P_1$ to $P_3$ and simultaneous paced ECGs can be stored in memory for later retrieval, or uploaded from a database 197 or interface 198. Alternatively, the input module 200 controls an off-line function whereby event-specific samples and paced morphologies can be analyzed without the presence of the patient. In all cases, electrograms must be aligned in time, using one of several approaches, to enable temporal correlations and spatial coherence to be assessed.

Second, the paced template is used to probe the sensed sequence, by using temporospatial correlation analysis to compare paced to sensed signals for corresponding ECG leads or electrogram channels. For example, paced ECG lead X (points $P_i$) is compared to lead X during the cardiac event (points $S_i$). This is then repeated for leads Y and Z. All of the analyses in mode B, including temporospatial correlation, spectral and eigenvector analyses are performed. If the ROVE catheter is placed close to the location of the arrhythmia circuit, the loops of $P_i$ versus $S_j$, as well as each being reproducible and narrow, will be similar to each other with principal axes that lie parallel to the line of identity. The invention provides precise time alignment, to allow loop axes to lie along this line of identity. Also, the invention will ensure that an equal number of cycles is examined even if one rhythm is faster than the other. This is done by choosing template durations that reflect the ratio of the longer cycle length (slower rhythm) to the shorter cycle length (faster rhythm). For example, if the cardiac event (say, monomorphic ventricular tachycardia) is 1.25 times faster than the paced rhythm (from the ROVE catheter), the duration of the cardiac event template will be made equal to 0.8 times (=1/1.25) the duration of the paced rhythm template (for example, 160 ms versus 200 ms, respectively). The number of correlation points will be identical between paced and cardiac event sequences by the uniform omission of points from the slower rate ECG or by linear interpolation of points into the faster rate ECG. Correlations of paced versus cardiac event ECGs will therefore examine comparable spatial phase despite cycles of different lengths.

Third, the above process is repeated by correlating sensed samples to the paced electrograms, and by correlating paced ECG templates against sensed ECGs of different orientations (such as paced lead X versus sensed lead Y), and by determining whether the XY, YZ and XZ loops are essentially superimposible for native versus paced sequences. Regions of slow conduction, indicated by deviations of temporospatial coherence from a uniform timing, are also used to help position the catheter. In process 645, the process controller 190 uses these analyses to determine the numerical difference between paced and event-specific samples. The difference is displayed in module 230 (FIG. 1B) and termed a good, indifferent or bad pace map. If good, then the text-label SITE is displayed.

4. Concealed Entrainment Module

The concealed entrainment module (FIG. 4, process 650) is only activated while the patient is experiencing the cardiac event of interest. It uses the principle of entrainment with concealed fusion to determine if the current pacing catheter, typically ROVE, is located close to the arrhythmia circuit.

Paced samples $P_1$ to $P_3$ are obtained in a slightly different manner than in the Pace Map module. Here, pacing occurs during the cardiac event, but at a slightly higher rate and shorter period (typically by 20–40 milliseconds). The process controller 190 operates the pacing module 160 to emit pacing signals from the ROVE catheter which, in the preferred embodiment, is an ablation electrode 138 (see FIG. 1B). The process controller 190 records and stores, in host processor 195, database 197 or via interface 198, surface ECG signals acquired from electrodes 130 and intracardiac signals from the ROVE catheter and intracardiac electrodes 134', 136 and 138. These electrodes must remain in the same position throughout analysis.

The invention now uses temporospatial correlations to determine the difference and similarity in ECG and intracardiac signals between pacing and the cardiac event. The invention compares paced electrogram samples $P_1$ to $P_3$ and the surface ECG to the analogous event-specific samples $S_1$ to $S_3$ and the ECG using the same electrodes. If correlation maps are dissimilar, the activation exit points between pacing and the cardiac event cannot be the same. The ROVE catheter is then moved closer to the arrhythmia circuit per the Catheter Guidance mode (mode D), described fully below.

As in the Pace-Map module, the invention will ensure precise time alignment and that template durations are proportional to rate differences between entrained and native rhythms. Since entrained (paced) rhythms are slightly faster than native rhythms (by design), entrained templates will be proportionally shorter. For example, if the entrained rhythm (from the ROVE catheter) is 1.1 times faster than the native rhythm (say, typical atrial flutter), then the duration of the entrained template will be made equal to 0.91 times (=1/1.1) the duration of the native rhythm template (for example, 227 ms versus 250 ms, respectively). The number of correlation points will be identical between paced and cardiac event sequences by the uniform omission of points from the slower rate ECG or by linear interpolation of points into the faster rate ECG. ECG correlations will therefore potentially span the same number of cycles to examine spatial phase for cycles of different cycle lengths.

Temporospatial correlation is used to perform the following component analyses of entrainment with concealed fusion (as per work by Waldo et al. [27] and Almendral et al. [31]):

1. Similarity of ECG morphologies between pacing and event-specific recordings;

2. Similarity of intracardiac electrogram morphologies between pacing and event-specific recordings. Monophasic action potential or unipolar intracardiac recordings facilitates this analysis.

3. Examination of the similarity between the post-pacing interval and the event-specific cycle length;

4. Similarity between stimulus to QRS and electrogram to QRS intervals;

5. Demonstration that the QRS and intracardiac electrogram complexes show progressive fusion with incrementally faster pacing.

Specifically, the following analyses are performed (FIG. 4, processes 650 to 660):

1. During the cardiac event, the duration of time between the electrogram on the ROVE catheter and the ECG complex corresponding to activation of that chamber. The time of activation is provided by the correlation loop take off, reducing errors commonly introduced when determining exact QRS onset from a noisy time-domain signal, for example.

2. During concealed entrainment pacing, the duration of time between the ROVE catheter electrogram and the start of surface ECG activation will also be determined as above in #1.

3. Demonstration that #1 and #2 are equivalent. This uses temporospatial correlation to establish an equivalent timing ('phase') between the electrogram to QRS (#1) and stimulus to QRS (#2) intervals during entrainment [27].

4. Compare the timing of the return of the ROVE catheter electrogram after the termination of pacing, with the timing of each cycle during the cardiac event of interest. This will be done using temporospatial correlation analysis. Demonstration that the post-pacing interval equals the tachycardia cycle length is a major criterion for entrainment [27].

5. With faster pacing, the invention will demonstrate that ECG temporospatial correlation loops lie on a progressive spectrum from event-specific to pacing-specific. This uses temporospatial correlation to demonstrate progressive fusion, as per Waldo et al. [27].

6. With faster pacing, demonstrate that temporospatial correlation loops from intracardiac electrograms at the ROVE catheter lie on a progressive spectrum between event-specific and paced. This demonstrates progressive electrogram fusion, as per Waldo et al. [27].

For a given ROVE catheter position, the invention uses these analyses to generate the indices described in Mode B that determine whether ROVE is close to the arrhythmia circuit. As summarized in FIG. 4, processes 650 and 660, the invention displays this information on the display component 230 in FIG. 1B.

D. Catheter Guidance System

Mode D (FIG. 4, process 665), Catheter Guidance System, operates as an adjunct to the Intracardiac Diagnosis and Arrhythmia Localization mode (mode C). In general, this mode determines the spatial plane of poorest correlation between paced and event-specific samples from the ROVE catheter. Analyses are then used to indicate to the user the direction in which to move ROVE catheter to improve this correlation and, therefore, improve contact with the arrhythmia circuit (see FIG. 9). This is used in two preferred operating modes (1) placement of an ablation catheter (electrode 138 in FIG. 1B) to deliver ablation energy; and (2) placement of an implanted catheter such as a pacemaker or implantable defibrillator lead, to deliver defibrillation energy or pacing impulses.

1. Placement of an Ablation Catheter

First, the invention determines the plane in which ECG correlations are poor when pacing from the ROVE catheter (at the rate of the cardiac event) and comparing the resulting electrograms to those during sensed signals from the cardiac event (FIG. 4, process 665), stored in the memory of the host processor 195 or uploaded 197, 198. The correlation and reproducibility indices described above are determined in the XY, YZ and XZ planes. Eigen vectors are used to determine whether the planes of maximal energy coincide between pacing and the cardiac event of interest.

By way of example, consider a ROVE catheter position from whence pacing produces ECGs whose correlation to the cardiac event match poorly in the YZ plane, but lies along the line of identity in the XY plane. The ROVE catheter is then moved parallel to the Z-axis (ECG lead V1). The direction in which to move the ROVE catheter is determined by signal polarity (FIG. 4, process 670). Since a wavefront moving towards an electrode generates a positive potential, if the paced ECG is more positive than the event for the V1 lead, ROVE must be moved away from V1 (i.e. away from the front of the chest) to get closer to the arrhythmia circuit. The opposite is also true. The invention calculates these comparisons for all leads simultaneously and displays them on module 230 as graphics and text MOVE V, where V is this vector of movement (FIG. 4, process 675). This lifts the burden of making multiple comparisons from the physician, and is also more accurate.

Second, once paced and sensed ECGs match, the catheter is moved even more precisely to the arrhythmia circuit by matching intracardiac signals. This is done using temporospatial correlation, and cross-correlation of electrogram shapes (morphologies), between paced samples, $P_i$, and event-specific samples, $S_i$, at all intracardiac electrodes 134', 136, ROVE. When the ROVE catheter lies at the exit point of the cardiac event of interest (SCZ in FIG. 9), pacing will cause exactly timed and very similarly shaped electrograms to those during the cardiac event at all intracardiac locations. In an alternative embodiment, pacing is performed from electrodes 134', 136 or 138. That electrode producing the closest electrogram correlations to the cardiac event is closest to a potential ablation site. The ROVE catheter is moved next to this electrode and then pacing is repeated from ROVE. This process continues until all intracardiac signals are correlation-matched between pacing from the ROVE catheter and the event. A minimum number of intracardiac electrodes must therefore be placed to optimize spatial resolution. In the preferred embodiment this includes electrodes in the coronary sinus, right atrium and His bundle position for atrial diagnosis and also at the right ventricular apex, and possibly cardiac veins, for ventricular diagnosis.

In the preferred embodiment, intracardiac signals are recorded in unipolar or monophasic action potential configurations. This enables electrogram shapes to be used to further confirm electrogram matches. An ideal shape match is characterized by maximal morphology cross-correlations between paced and sensed signals. Many cross-correlation coefficients can be used, such as the Pearson and Fischer methods. For this stage, the ROVE catheter is moved as before, electrogram shapes are compared by cross-correlation after each pacing intervention, as well as temporospatial correlation analysis.

When temporospatial correlation and morphology correlation indicates a precise match between ROVE and the arrhythmia circuit, within acceptable biologic tolerances, the text label SITE is displayed 230 (FIG. 4, process 690). The physician will typically perform ablation at this site. However, this process may also be used to locate the arrhythmia tissue to deliver electrical defibrillation (an electrical shock) or other modulation (such as delivering pharmaceuticals, cells or genes).

The described here improves upon the cross-correlation method in U.S. Pat. No. 5,792,064 issued to Panescu. Panescu et al. analyze one single beat, especially the beat that initiates AF, while this invention analyzes a continuous arrhythmia tracing using temporospatial morphology correlation (on electrograms as well as ECGs) to extract atrial versus ventricular features. In addition, Panescu et al. analyzed only the signal shape, while this invention fully and rigorously analyzes the activation sequence and timing of all signals. Their method is therefore less well-suited to analyze sustained tachycardia, for confirming a diagnosis, or for confirming the success of ablation (which will be discussed later).

2. Placement of Pacemaker or Implantable Defibrillator Lead.

This module is very similar to the above module. Since the cardiac event of interest will typically have arisen before device implantation, its ECG and intracardiac signals are typically uploaded from memory, the database 197 or an external interface 198.

Since the maneuverability of an implantable lead is lower than of an ablation electrode, even using guiding stylets, the operator may elect to rely upon ECG localization in this mode. However, the full benefits of intracardiac analysis are also available, if desired. As above, temporospatial correlations are performed to detect differences in activation pattern and shape between the current ROVE (typically the implanted lead) and cardiac event electrograms. When correlations match, the display module 230 indicates the text label SITE (FIG. 4, process 690), and the pacing or defibrillation lead is fixed in this position, preferably by an active fixation method such as screwing the lead into the myocardium in standard fashion. In an alternative implementation, a more maneuverable ablation catheter (ROVE) is first directed to locate the arrhythmia site, and the implantable lead is then moved adjacent to that catheter.

In an alternative embodiment, the invention can be used in conjunction with an intracardiac anatomic mapping system, such as that made by Biosense-Webster, Inc. (Diamond Bar, Calif.), described in the prior art by U.S. Pat. No. 5,568,809 issued to Ben-Haim, or Endocardial Solutions, Inc. (St. Paul, Minn.). In this embodiment, the ROVE catheter position is known at all times to the mapping system. ECG analyses are then performed to improve upon spatial localization using entrainment and pace-mapping functional data.

E. Determination of Ablation Success

This mode is shown in FIG. 4, processes 695–705. The process controller 190 determines that successful ablation has been achieved if pacing from the ROVE catheter at the ablation site can no longer reproduce prior correlation maps or electrogram morphologies. The rationale for this approach is that tissue ablated in or close to the slow conduction zone, SCZ in FIG. 9, prevents subsequent depolarization. The destroyed tissue is thereby "closed" as a possible path of propagation. Since depolarization events bypass the ablated region and no longer become caught in circus motion, ablation restores normal heart function. Similarly, electrograms following pacing at this site will now cause different temporospatial correlation.

Following ablation, the process controller 190 conditions the pacing module 160 to pace the heart using the ROVE electrode at the cycle length of the cardiac event. Intracardiac electrograms 134', 136, 138 and ECG signals 130 are recorded using the recording components 150 and 158. The process controller 190 and host processor 195 perform temporospatial correlation and the other analyses above, and compare the results between pre- and post-ablation at this position.

In one implementation, the host processor 195 sets a numeric threshold B for these analyses. A higher index, indicating similarity of activation before versus after ablation, indicates a high probability that the arrhythmia circuit is still present. Since the Catheter Guidance Mode (mode D) is automatically engaged during pacing, if correlations remain high then proximity criteria are again met, and the host processor 195 will display 230 the text-label SITE. A repeat attempt at ablation may be performed at this site.

Successful ablation is indicated if the correlation between pre- and post-ablation pacing is low for the same electrode position. If this occurs, the system recommends that the physician move the ROVE catheter slightly and repeat the analysis. This is repeated for slight ROVE movements along each vector. If correlations remain poor, then the procedure is completed by attempting to re-induce the cardiac event. This is routinely performed in the prior art. If the event can also no longer be re-induced, the invention determines that there is a very high likelihood that the event arrhythmia has been successfully ablated.

F. Arrhythmia Prediction

This mode (FIG. 4, processes 710 to 750) detects the substrates for atrial or ventricular arrhythmias by detecting variability in temporospatial correlations during progressively faster pacing. The rationale for this approach is as follows. During heart rate acceleration in the presence of substrates, atrial or ventricular recovery will eventually be unable to keep up with activation, and subsequent activation will split into two or more distinct populations. From the prior art, incremental pacing at the right ventricle encroaches upon its recovery, causing T-wave alternans. This was previously detected using spectral decomposition in U.S. Pat. No. 4,802,491 issued to Cohen and U.S. Pat. No. 5,148,812 issued to Verrier. The present invention provides a new means of showing T-wave alternans, as a bifurcation into two distinct T-wave temporospatial correlation loops. However, this invention can also similarly demonstrate alternans of atrial intracardiac signals, which have recently been shown to predict AF from work by Narayan et al. [20].

The process controller 190 conditions the pacing module 160 to emit pacing signals to the trans-esophageal electrode 136 or an intracardiac electrode 134' or 138. The recording components 150 and 158 record the surface ECG from electrodes 130, as well as intracardiac signals from the above electrodes, at user-specified and stored paper (sweep) speed and electrogram gain. Pacing is performed for 10 or more seconds at each rate. The process controller 190 performs correlation analysis at each pacing rate at this site. Since there is no prior cardiac arrhythmia event, the process controller 190 stores pacing correlation maps for each progressive rate at the same pacing site in the heart 110 on the host processor 195, or database 197, then compares them against each other as above.

In one implementation, a high likelihood for the presence of an arrhythmia circuit, is indicated by poor reproducibility of temporospatial correlations, an (alternating) fluctuation in the Eigen vector of the specific waveform of interest (such as atrial activity, or ventricular T-wave repolarization), or variability in the principal axis slopes of successive correlation loops. This is shown in processes 730 to 750. It must be stressed that this analysis cannot be performed at excessive heart rates, since bifurcation may occur in normal individuals at rates above 110 beats per minute (cycle length 545 milliseconds) for ventricular pacing, and 250 beats per minute (cycle length 240 milliseconds) for the atrium. By contrast, highly reproducible correlations indicate a low risk (processes 740 to 750). Intermediate risk is assigned to the presence of some of the above metrics.

The implementation of the system described herein is based largely upon digital signal processing techniques. However, it should be appreciated that a person of ordinary skill in this technology area can easily adapt the digital techniques for analog signal processing.

While the invention has been described in connection with preferred embodiments, they are not intended to limit the scope of the invention to the particular form set forth, but on the contrary, they are intended to cover such alternatives, modifications, and equivalents as may be included within the spirit and scope of the invention as defined by the appended claims.

REFERENCES

1. Horvath, G., J. J. Goldberger, and A. H. Kadish, *Simultaneous occurrence of atrial fibrillation and atrial flutter.* J. Cardiovascular Electrophysiol., 2000. 11(8): p. 849–858.

2. Tang, C. W., M. M. Scheinman, G. F. Van Hare, L. M. Epstein, A. P. Fitzpatrick, R. J.

Lee, et al., *Use of P Wave Configuration During Atrial Tachycardia to Predict Site of Origin.* Journal of the American College of Cardiology, 1995. 26(5): p. 1315–1324.

3. Xue, Q. and S. Reddy, *Algorithms for computerized QT analysis.* J. Electrocardiol., 1998. 30: p. 181–186.

4. Yamane, T., D. C. Shah, J.-T. Peng, P. Jais, M. Hocini, I. Deisenhofer, et al., *Morphological characteristics of P waves during selective pulmonary vein pacing.* Journal of the American College of Cardiology, 2001. 38(5): p. 1505–1510.

5. SippensGroenewegen, A., M. D. Mlynash, F. X. Roithinger, Y. Goseki, and M. D. Lesh, *Electrocardiographic Analysis of Ectopic Atrial Activity Obscured by Ventricular Repolarization: P Wave Isolation Using an Automatic 62-Lead QRST Subtraction Algorithm.* J. Cardiovascular Electrophysiol., 2001. 12: p. 780–790.

6. Brugada, P., J. Brugada, L. Mont, J. Smeets, and E. W. Andries, *A New Approach to the Differential Diagnosis of a regular tachycardia with a wide QRS complex.* Circulation, 1991. 83: p. 1649–1659.

7. Callans, D. J., V. Menz, D. Schwartzman, C. D. Gottlieb, and F. E. Marchlinski, *Repetitive monomorphic tachycardia from the left ventricular outflow tract: electrocardiographic patterns consistent with a left ventricular site of origin.* J. Am. Coll. Cardiol., 1997. 29(1023–1027).

8. Peeters, H. A. P., A. SippensGroenewegen, B. A. Schoonderwoerd, E. F. D. Wever, C. A. Grimbergen, R. N. W. Hauer, et al., *Body-Surface QRST Integral Mapping: Arrhythmogenic Right Ventricular Dysplasia Versus Idiopathic Right Ventricular Tachycardia*, in Circulation. 1997. p. 2668–2676.

9. Stambler, B. S. and K. A. Ellenbogen, *Elucidating the Mechanisms of Atrial Flutter Cycle Length Variability Using Power Spectral Analysis Techniques*, in Circulation. 1996b. p. 2515–2525.

10. Zhang, X.-S., Y.-S. Zhu, N. V. Thakor, and Z.-Z. Wang, *Detecting Ventricular Tachycardia and Fibrillation by Complexity Measure*. IEEE Transactions in Biomedical Engineering, 1999. 46(5): p. 548–555.

11. Lau, C.-P., *Radiofrequency Ablation of fascicular Tachycardia: efficacy of pace-mapping and implications on tachycardia origin*. International Journal of Cardiology, 1994. 46: p. 255–265.

12. Morton, J. B., P. Sanders, V. Deen, J. K. Vohra, and J. M. Kalman, *Sensitivity and specificity of concealed entrainment for the identification of a critical isthmus in the atrium: relationship to rate, anatomic location and antidromic penetration*. Journal of the American College of Cardiology, 2002. 39(5): p. 896–906.

13. Stevenson, W. G., H. Khan, P. Sager, et al., *Identification of reentry circuit sites during catheter mapping and radiofrequency ablation of ventricular tachycardia late after myocardial infarction*. Circulation, 1993. 88: p. 1647–1670.

14. Hamdan, M. H., J. M. Kalman, H. V. Barron, and M. D. Lesh, *P-Wave Morphology During Right Atrial Pacing Before and After Atrial Flutter Ablation—A New Marker for Success*. The American Journal of Cardiology, 1997. 79(10): p. 1417–1420.

15. Villacastin, J., J. Almendral, A. Arenal, N. P. Castellano, S. Gonzalez, M. Ortiz, et al., *Usefulness of Unipolar Electrograms to Detect Isthmus Block After Radiofrequency Ablation of Typical Atrial Flutter*, in Circulation. 2000. p. 3080–3085.

16. Tada, H., H. Oral, C. Sticherling, S. P. Chough, R. L. Baker, K. Wasmer, et al., *Double potentials along the ablation line as a guide to radiofrequency ablation of typical atrial flutter*. Journal of the American College of Cardiology, 2001. 38(3): p. 750–755.

17. LeClercq, C., F. Victor, C. Alonso, D. Pavin, G. Revault d'Allones, J. Y. Bansard, et al., *Comparative effects of permanent biventricular pacing for refractory heart failure in patients with stable sinus rhythm or chronic atrial fibrillation*. The American Journal of Cardiology, 2000. 85(9): p. 1154–1156.

18. Zagrodzky, J. D., K. Ramaswamy, R. L. Page, J. A. Joglar, C. J. Sheehan, M. L. Smith, et al., *Biventricular pacing decreases the inducibility of ventricular tachycardia in patients with ischemic cardiomyopathy*. The American Journal of Cardiology, 2001. 87(10): p. 1208–1210.

19. Steinberg, J. S., Z. Zelenkofske, S. C. Wong, et al., *The value of the P-wave signal-averaged electrocardiogram for predicting atrial fibrillation after cardiac surgery*. Circulation, 1993a. 88: p. 2618.

20. Narayan, S. M., F. Bode, P. L. Karasik, and M. R. Franz, *Alternans Of Atrial Action Potentials As A Precursor Of Atrial Fibrillation*. Circulation, 2002b. 106: p. 1968–1973.

21. Kleiger, R. E., P. Millar, J. T. Bigger, et al., *Decreased heart rate variability and its association with increased mortality after acute myocardial infarction*. Am. J. Cardiol., 1987. 59: p. 256–262.

22. Simson, M. B., *Identification of patients with ventricular tachycardia after myocardial infarction from signals in the terminal QRS complex*. Circulation, 1981a. 64: p. 235–42.

23. Feld, G. K., R. P. Fleck, P. S. Chen, K. Boyce, T. D. Bahnson, J. B. Stein, C. M. Calisi, M. Ibarra, *Radiofrequency catheter ablation for the treatment of human type I atrial flutter: Identification of a critical zone in the reentrant circuit by endocardial mapping techniques*. Circulation, 1992. 86: p. 1233–1240.

24. Jackman, W. M., K. J. Beckman, J. H. McClelland, et al., *Treatment of supraventricular tachycardia due to atrioventricular nodal reentry by radiofrequency catheter ablation of slow-pathway conduction*. N Engl J Med, 1992. 327: p. 313–318.

25. Watanabe, K., V. Bhargava, and V. Froelicher, *Computer Analysis of the Exercise ECG: A Review*. Prog. Cardiovasc. Dis., 1980. 22(6): p. 423–446.

26. Saba, S., G. Feld, S. Yang, D. MacAdam, W. Su, M. S. Link, M. K. Homoud, C. Foote, N. A. M. Estes, P. J. Wang, *Testing of a new real-time computer algorithm as an aid to pace mapping and entrainment with concealed fusion*. The American Journal of Cardiology, 2001. 87(11): p. 1301–1305.

27. Waldo, A., W. MacClean, R. Karp, N. Kouchoukos, and T. James, *Entrainment and interruption of atrial flutter with atrial pacing; studies in man following open heart surgery*. Circulation, 1977. 56: p. 737–45.

28. Henthorn, R., K. Okumura, B. Okumura, B. Olshansky, V. Plumb, P. Hess, et al., *A fourth criterion for transient entrainment: the electrogram equivalent of progressive fusion*. Circulation, 1988. 77: p. 1003–1012.

29. Bloomfield, D. M., S. H. Hohnloser, and R. J. Cohen, *Interpretation and Classification of Microvolt T-Wave Alternans Tests*. J. Cardiovascular Electrophysiol., 2002. 13(5): p. 502–512.

30. Rosenbaum, D. S., L. E. Jackson, J. M. Smith, H. Garan, J. N. Ruskin, and R. J. Cohen, *Electrical alternans and vulnerability to ventricular arrhythmias*. New England Journal of Medicine, 1994. 330(4): p. 235-91.

31. Almendral J M, Gottlieb C D, Rosenthal M E, Stamato N J, Buxton A E, Marchlinski F E, Miller J M, Josephson M E, Entrainment of Ventricular Tachycardia: Explanation for Surface Electrocardiographic Phenomena by Analysis of Electrograms Recorded Within the Tachycardia Circuit. Circulation, 1988. 77(3): p. 569–580.

What is claimed is:

1. A method of analyzing a cardiac signal, comprising:
    providing a digital template and a digitized cardiac signal with sufficient fidelity and resolution to facilitate identification of atrial fibrillatory components of activity from distinct regions of the heart and further having sufficient fidelity and resolution to facilitate identification of the atrial fibrillatory components as originating from a left side or a right side of the heart, the identification being sufficient to facilitate a separation of atrial tachycardia, atrial fibrillation, atrial flutter and ventricular tachycardia, the digitized cardiac signal comprising a plurality of amplitudes corresponding to consecutive time samples, wherein the time samples span a plurality of cardiac cycles;
    generating a plurality of correlation values correlating the digital template to successive time samples of the cardiac signal, wherein a plurality of correlation values are generated for each cardiac cycle that contain information necessary to identify and differentiate distinct components of activity and to discern whether those components have origins in the left or right sides of the heart;
    mapping the correlation values; and
    identifying a treatable disease, based upon the mapping of the correlation values.

2. The method as set forth in claim 1, wherein the correlation values are mapped against time.

3. The method as set forth in claim 1, wherein the correlation values are plotted.

4. The method as set forth in claim 1, wherein successive time samples are consecutive time samples.

5. The method as set forth in claim 1, wherein the cardiac signal is an ECG.

6. The method as set forth in claim 1, wherein the cardiac signal is an intracardiac electrogram.

7. The method as set forth in claim 1, and thither comprising computing at least one Eigen vector.

8. The method as set forth in claim 1, and further comprising:
comparing correlation values with a threshold value; and
identifying features as correlation values that exceed the threshold value.

9. The method as set forth in claim 8, and further comprising defining features from the correlation values.

10. The method as set forth in claim 9, wherein the features comprise activity from distinct regions of cardiac chambers.

11. The method as set forth in claim 9, wherein the features comprise activity from an atrium.

12. The method as set forth in claim 9, wherein the features comprise activity from a ventricle.

13. The method as set forth in claim 9, wherein the features comprise repolarization.

14. The method as set forth in claim 1, and further comprising generating frequency representation of the digitized cardiac signal and of the correlation values.

15. The method as set forth in claim 14, wherein the frequency representation of the digitized cardiac signal comprises a plot of frequency versus power.

16. The method as set forth in claim 14, and further comprising identifying an non-harmonic frequencies having relatively low amplitudes.

17. The method as set forth in claim 14, wherein the frequency representation of the digitized cardiac signal comprises a plot of frequency versus power and wherein the identified non-harmonic frequencies have power amplitudes which are less than about 1/10 of a maximum power amplitude of the frequency representation.

18. The method as set forth in claim 17, and further comprising:
generating a time-domain representation of a selected band of the frequency representation; and
identifying a feature, based upon the time-domain representation.

19. The method as set forth in claim 18, wherein the feature represents intracardiac timing.

20. The method as set forth in claim 19, wherein the feature represents intracardiac timing of atrial arrhythmia.

21. The method as set forth in claim 20, wherein the feature represents intracardiac timing of irreguiar atrial arrhythmia.

22. The method as set forth in claim 19, wherein the feature represents intracardiac timing of ventricular arrhythmia.

23. The method as set forth in claim 22, wherein the feature represents intracardiac timing of irregular ventricular arrhythmia.

24. The method as set forth in claim 14, wherein the frequency representation of the correlation values comprises a plot of frequency versus power and wherein the identified non-harmonic frequencies have power amplitudes which less than about 1/10 of a maximum power amplitude of the frequency representation.

25. The method as set forth in claim 24, and further comprising:
generating a time-domain representation of a selected band of the frequency representation; and
identifying a feature, based upon the time-domain representation.

26. The method as set forth in claim 1, and wherein:
the cardiac signal is generated from a plurality of leads; and
the correlation values are plotted, each plot comprising a representation of correlation values of two leads from the plurality of leads, for each plot the correlation values of one of the two leads being plotted against the correlation values of the other of the two leads.

27. The method as set forth in claim 26, wherein the plurality of leads comprises at least three leads, and the correlation values are plotted to yield plots for a plurality of planes.

28. The method as set forth in claim 27, and further comprising identifying a coherence of spatial phase for at least one of the three plots, when correlation values for that plot rise and fall simultaneously for both axes of that plot.

29. The method as set forth in claim 27, and further comprising identifying a coherence of spatial phase for the three plots, when correlation values for each of the three plots rise and fall simultaneously for both axes of each of the three plots.

30. The method as set forth in claim 29, and further comprising:
comparing correlation values for each plot with a threshold value; and
identifying features as correlation values that exceed the threshold value.

31. The method as set forth in claim 26, wherein the plurality of leads comprises at least three orthogonal leads, and the correlation values are plotted to yield three plots for three corresponding orthogonal planes.

32. The method as set forth in claim 1, wherein the amplitudes are electrical potential.

33. The method as set forth in claim 1, wherein the amplitudes represent tracings corresponding to electrical activity from organs other than the heart.

34. The method as set forth in claim 1, and wherein the digital template is a sequence of amplitudes spanning part of a cardiac cycle.

35. The method as set forth in claim 1, and wherein:
the cardiac signal is generated from a plurality of leads;
for each of at least three of the plurality of leads, a mapping of correlation values is generated so that at least three mappings of correlation values are generated; and
the method further comprises identifying alternans of mappings.

36. The method as set forth in claim 35, wherein the alternans comprise cycles of correlation that alternate for successive heartbeats.

37. The method as set forth in claim 1, and wherein:
the cardiac signal is generated from a plurality of leads;
for each of at least three of the plurality of leads, a mapping of correlation values is generated so that at least three mappings of correlation values are generated; and
the method further comprises identifying the mapping, which has a poorest correlation with the other mappings.

38. The method as set forth in claim 1, and wherein the providing is preceded by:
   (a) placing a medical instrument into proximity of a heart;
   (b) stimulating the heart using the medical instrument to generate a paced cardiac signal;
   (c) selecting at least three spatial axes and, for each of the spatial axes, determining a correlation of the cardiac signal to the paced cardiac signal;
   (d) identifying a spatial axis of the at least three spatial axes that has a lowest determined correlation; and
   (e) moving the medical instrument in a direction of the identified axis.

39. The method as set forth in claim 38, wherein the moving comprise moving the medical instrument along the identified axis.

40. The method as set forth in claim 38, wherein the moving improves the lowest determined correlation.

41. The method as set forth in claim 40, and further comprising repeating (c), (d) and (e).

42. The method as set forth in claim 40, wherein the identified spatial axis for one occurrence of (c), (d) and (e) is different than an identified spatial axis for another occurrence of (c), (d) and (e).

43. The method as set forth in claim 1, and wherein the providing is preceded by:
   placing a medical instrument into proximity of a heart;
   stimulating the heart using the medical instrument to generate a paced cardiac signal;
   the cardiac signal is generated from a plurality of leads;
   for each of at least three of the plurality of leads, a mapping of correlation values is generated so that at least three cardiac mappings of correlation values are generated;
   the paced cardiac signal is generated from a plurality of leads;
   for each of at least three of the plurality of leads, a mapping of correlation values is generated for the paced cardiac signal so that at least three paced-cardiac mappings of correlation values are generated for the paced cardiac signal; and
   identifying a paced-cardiac mapping of the at least three paced-cardiac mappings that correlates poorest with a mapping of the at least three cardiac mappings.

44. The method as set forth in claim 43, wherein the identifying comprises identifying a paced-cardiac mapping of the at least three paced-cardiac mappings that correlates poorest with a corresponding mapping of the at least three cardiac mappings.

45. The method as set forth in claim 44, wherein the correlation of the identified paced-cardiac mapping with the corresponding cardiac mapping is improved.

46. The method as set forth in claim 43, wherein:
   each mapping of the at least three cardiac mappings corresponds to a spatial axis;
   each mapping of the at least three paced-cardiac mappings corresponds to the spatial axis;
   the identifying comprises identifying the spatial axis corresponding to the identified paced-cardiac mapping; and
   the identifying is followed by moving the medical instrument in a direction of the identified spatial axis.

47. The method as set forth in claim 46, wherein the moving comprise moving the medical instrument along the identified axis.

48. The method as set forth in claim 1, wherein the cardiac signal is a biopotential of a cardiac arrhythmia.

49. The method as set forth in claim 48, wherein the cardiac arrhythmia comprises one of ventricular tachycardia, atrial tachycardia, atrial flutter and atrial fibrillation.

50. The method as set forth in claim 49, wherein the cardiac arrhythmia comprises ventricular tachycardia.

51. The method as set forth in claim 49, wherein the cardiac arrhythmia comprises atrial tachycardia.

52. The method as set forth in claim 49, wherein the cardiac arrhythmia comprises atrial flutter.

53. The method as set forth in claim 49, wherein the cardiac arrhythmia comprises atrial fibrillation.

54. The method as set forth in claim 1, wherein the identification comprises separating and analyzing the distinct components of activity.

55. The method as set forth in claim 1, wherein the cardiac signal is a biopotential of a cardiac arrhythmia.

56. The method as set forth in claim 55, wherein the distinct components of activity include atrial and ventricular activity.

57. The method as set forth in claim 55, wherein the distinct components of activity include activation and repolarization.

58. The method as set forth in claim 55, wherein the distinct components of activity include activity from distinct regions of cardiac chambers.

59. The method as set forth in claim 55, wherein the distinct components of activity include activity from separate functional units within cardiac chambers.

60. The method as set forth in claim 55, wherein:
   the identification comprises separating distinct components of activity; and
   the separating comprises separating atrial tachycardia, atrial fibrillation, atrial flutter and ventricular tachycardia.

61. The method as set forth in claim 1, wherein the amplitudes represent tracings corresponding to non-electrical activity.

* * * * *